US011819666B2

(12) United States Patent
Bar-El et al.

(10) Patent No.: US 11,819,666 B2
(45) Date of Patent: Nov. 21, 2023

(54) MODULAR DRIVE TRAIN FOR WEARABLE INJECTOR

(71) Applicant: West Pharma. Services IL, Ltd., Ra'anana (IL)

(72) Inventors: Yossi Bar-El, Beit Arye (IL); Gil Yigal, Gan Yavne (IL); Reuven Y. Filman, Tel Mond (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 945 days.

(21) Appl. No.: 16/618,345

(22) PCT Filed: May 25, 2018

(86) PCT No.: PCT/US2018/034597
§ 371 (c)(1),
(2) Date: Nov. 30, 2019

(87) PCT Pub. No.: WO2018/222521
PCT Pub. Date: Dec. 6, 2018

(65) Prior Publication Data
US 2021/0138157 A1     May 13, 2021

Related U.S. Application Data

(60) Provisional application No. 62/512,505, filed on May 30, 2017.

(51) Int. Cl.
*A61M 5/315* (2006.01)
*A61M 5/31* (2006.01)

(52) U.S. Cl.
CPC . *A61M 5/31511* (2013.01); *A61M 2005/3142* (2013.01); *A61M 2005/3152* (2013.01); *A61M 2005/31518* (2013.01)

(58) Field of Classification Search
CPC ............ A61M 5/31511; A61M 5/31576; A61M 5/20; A61M 5/2053; A61M 5/31505;
(Continued)

(56) References Cited

U.S. PATENT DOCUMENTS

| 232,432 A | 9/1880 | Allison |
| 1,125,887 A | 1/1915 | Schimmel |

(Continued)

FOREIGN PATENT DOCUMENTS

| CA | 832729 | 1/1970 |
| CA | 2832729 A1 | 10/2012 |

(Continued)

OTHER PUBLICATIONS

US 8,333,733 B2, 12/2012, Lanigan et al. (withdrawn)
(Continued)

*Primary Examiner* — Jason E Flick
*Assistant Examiner* — Justin L Zamory
(74) *Attorney, Agent, or Firm* — Blank Rome LLP

(57) ABSTRACT

A modular drive train is selectively securable within a wearable injector. The drive train includes a chassis and a telescoping driving assembly mounted within the chassis. The driving assembly includes a first shaft rotatable relative to the chassis, and a second shaft connected with the first shaft and axially movable relative thereto. Rotation of the first shaft axially drives the second shaft. The chassis includes one of a bearing and an elastically expandable collar projecting axially forward into the chassis from a rear end thereof, and the first shaft includes the other of the bearing and the elastically expandable collar projecting axially rearwardly from a rear end thereof. The collar is configured to elastically snap over an interference element of the bearing, whereby engagement of the collar with the
(Continued)

bearing axially secures the first shaft to the chassis and permits rotation of the first shaft about the bearing.

23 Claims, 6 Drawing Sheets

(58) Field of Classification Search
CPC ............ A61M 5/1452; A61M 5/14566; A61M 2005/3152; A61M 2005/31518; A61M 2005/14268; A61M 2005/31588; A61M 2205/8206
See application file for complete search history.

(56) References Cited

U.S. PATENT DOCUMENTS

| | | |
|---|---|---|
| 1,321,550 A | 11/1919 | Platt |
| 1,704,921 A | 3/1929 | Nicoll |
| 1,795,530 A | 3/1931 | Cowan |
| 1,795,630 A | 3/1931 | Wilson |
| 2,453,590 A | 11/1948 | Poux |
| 2,589,426 A | 3/1952 | Ogle |
| 2,677,373 A | 5/1954 | Barradas |
| 2,702,547 A | 2/1955 | Glass |
| 2,860,635 A | 11/1958 | Wilburn |
| 3,002,754 A | 10/1961 | Dombrowski |
| 3,203,269 A | 8/1965 | Perrine |
| 3,212,685 A | 10/1965 | Swan |
| 3,585,439 A | 6/1971 | Schneeberger |
| 3,623,474 A | 11/1971 | Heilman |
| 3,689,748 A | 9/1972 | Bothne |
| 3,705,582 A | 12/1972 | Stumpf |
| 3,708,945 A | 1/1973 | Klettke |
| 3,782,365 A | 1/1974 | Pinna |
| 3,794,028 A | 2/1974 | Mueller |
| 3,834,387 A | 9/1974 | Brown |
| 3,946,732 A | 3/1976 | Hurscham |
| 3,994,295 A | 11/1976 | Wulff |
| 4,026,128 A | 5/1977 | Blanco |
| 4,082,094 A * | 4/1978 | Dailey ............... A61M 39/1011 604/93.01 |
| 4,085,747 A | 4/1978 | Lee |
| 4,126,132 A | 11/1978 | Portner |
| 4,167,663 A | 9/1979 | Granzow, Jr. |
| 4,189,065 A | 2/1980 | Herold |
| 4,195,636 A | 4/1980 | Behnke |
| 4,218,724 A | 8/1980 | Kaufman |
| 4,222,380 A | 9/1980 | Terayama |
| 4,241,381 A | 12/1980 | Cobaugh |
| 4,254,768 A | 3/1981 | Ty |
| 4,270,537 A | 6/1981 | Romaine |
| 4,273,122 A | 6/1981 | Whitney |
| 4,276,879 A | 7/1981 | Yiournas |
| 4,300,554 A | 11/1981 | Hessberg |
| 4,322,668 A | 3/1982 | Trussler |
| 4,324,262 A | 4/1982 | Hall |
| 4,396,385 A | 8/1983 | Kelly |
| 4,403,987 A | 9/1983 | Gottinger |
| 4,425,120 A | 1/1984 | Sampson |
| 4,435,173 A | 3/1984 | Siposs |
| 4,465,478 A | 8/1984 | Sabelman |
| 4,497,036 A | 1/1985 | Dunn |
| 4,502,488 A | 3/1985 | Degironimo |
| 4,504,263 A | 3/1985 | Steuer |
| 4,549,554 A | 10/1985 | Markham |
| 4,564,054 A | 1/1986 | Gustavsson |
| 4,565,543 A | 1/1986 | Bekkering |
| 4,583,974 A | 4/1986 | Kokernak |
| 4,585,439 A | 4/1986 | Michel |
| 4,599,082 A | 7/1986 | Grimard |
| 4,601,702 A | 7/1986 | Hudson |
| 4,634,426 A | 1/1987 | Kamen |
| 4,636,201 A | 1/1987 | Ambrose |
| 4,645,326 A | 2/1987 | Kiuchi |
| 4,664,654 A | 5/1987 | Strauss |
| 4,667,299 A | 5/1987 | Dunn |
| 4,685,903 A | 8/1987 | Cable |
| 4,689,043 A | 8/1987 | Bisha |
| 4,695,274 A | 9/1987 | Fox |
| 4,698,055 A | 10/1987 | Sealfon |
| 4,702,738 A | 10/1987 | Spencer |
| 4,704,105 A | 11/1987 | Adorjan |
| 4,710,178 A | 12/1987 | Henri |
| 4,729,208 A | 3/1988 | Galy |
| 4,735,311 A | 4/1988 | Lowe |
| 4,737,144 A | 4/1988 | Choksi |
| 4,772,272 A | 9/1988 | McFarland |
| 4,781,688 A | 11/1988 | Thoma |
| 4,810,215 A | 3/1989 | Kaneko |
| 4,810,249 A | 3/1989 | Haber |
| 4,813,426 A | 3/1989 | Haber |
| 4,840,185 A | 6/1989 | Hernandez |
| 4,850,966 A | 7/1989 | Grau |
| 4,861,341 A | 8/1989 | Woodburn |
| 4,863,434 A | 9/1989 | Bayless |
| 4,867,743 A | 9/1989 | Vaillancourt |
| 4,874,383 A | 10/1989 | McNaughton |
| 4,882,575 A | 11/1989 | Kawahara |
| 4,886,499 A | 12/1989 | Cirelli |
| 4,892,521 A | 1/1990 | Laico |
| 4,897,083 A | 1/1990 | Martell |
| 4,900,310 A | 2/1990 | Ogle, II |
| 4,908,014 A | 3/1990 | Kroyer |
| 4,915,702 A | 4/1990 | Haber |
| 4,919,569 A | 4/1990 | Wittenzelliner |
| 4,919,596 A | 4/1990 | Slate |
| 4,923,446 A | 5/1990 | Page |
| 4,929,241 A | 5/1990 | Kulli |
| 4,950,235 A | 8/1990 | Slate |
| 4,950,241 A | 8/1990 | Ranford |
| 4,950,246 A | 8/1990 | Muller |
| 4,957,490 A | 9/1990 | Byrne |
| 4,964,866 A | 10/1990 | Szwarc |
| 4,994,045 A | 2/1991 | Ranford |
| 4,998,924 A | 3/1991 | Ranford |
| 5,019,051 A | 5/1991 | Hake |
| 5,034,004 A | 7/1991 | Crankshaw |
| 5,051,109 A | 9/1991 | Simon |
| 5,062,828 A | 11/1991 | Waltz |
| D322,671 S | 12/1991 | Szwarc |
| 5,088,988 A | 2/1992 | Talonn |
| 5,089,783 A | 2/1992 | Kapsokavathis |
| 5,090,877 A | 2/1992 | D Silva |
| 5,097,122 A | 3/1992 | Colman |
| 5,107,685 A | 4/1992 | Kobayashi |
| 5,109,850 A | 5/1992 | Blanco |
| 5,112,317 A | 5/1992 | Michel |
| 5,114,406 A | 5/1992 | Gabriel |
| 5,127,910 A | 7/1992 | Talonn |
| 5,131,816 A | 7/1992 | Brown |
| 5,147,326 A | 9/1992 | Talonn |
| 5,156,599 A | 10/1992 | Ranford |
| 5,190,521 A | 3/1993 | Hubbard |
| 5,211,638 A | 5/1993 | Dudar |
| 5,217,437 A | 6/1993 | Talonn |
| 5,246,670 A | 9/1993 | Haber |
| 5,254,096 A | 10/1993 | Rondelet |
| 5,267,977 A | 12/1993 | Feeney, Jr. |
| 5,269,762 A | 12/1993 | Armbruster |
| 5,275,582 A | 1/1994 | Wimmer |
| 5,282,593 A | 2/1994 | Fast |
| 5,295,966 A | 3/1994 | Stern et al. |
| 5,298,023 A | 3/1994 | Haber |
| 5,300,045 A | 4/1994 | Plassche, Jr. |
| 5,318,522 A | 6/1994 | D Antonio |
| 5,338,311 A | 8/1994 | Mahurkar |
| 5,342,313 A | 8/1994 | Campbell |
| 5,346,086 A | 9/1994 | Harris |
| 5,348,543 A | 9/1994 | Talley |
| 5,348,544 A | 9/1994 | Sweeney |
| 5,354,287 A | 10/1994 | Wacks |
| 5,364,364 A | 11/1994 | Kasvikis |
| 5,366,498 A | 11/1994 | Brannan |
| 5,376,785 A | 12/1994 | Chin |

(56) References Cited

U.S. PATENT DOCUMENTS

| | | |
|---|---|---|
| 5,383,865 A | 1/1995 | Michel |
| D356,150 S | 3/1995 | Duggan |
| 5,411,482 A | 5/1995 | Campbell |
| 5,415,645 A | 5/1995 | Friend |
| 5,430,636 A | 7/1995 | Kachi |
| 5,445,621 A | 8/1995 | Poli |
| 5,456,360 A | 10/1995 | Griffin |
| 5,478,315 A | 12/1995 | Brothers |
| 5,478,316 A | 12/1995 | Bitdinger |
| 5,482,446 A | 1/1996 | Williamson |
| 5,496,274 A | 3/1996 | Graves |
| 5,501,665 A | 3/1996 | Jhuboo |
| 5,505,709 A | 4/1996 | Funderburk |
| 5,527,287 A | 6/1996 | Miskinyar |
| D372,098 S | 7/1996 | Lattin |
| 5,558,639 A | 9/1996 | Gangemi |
| 5,562,624 A | 10/1996 | Righi |
| 5,562,686 A | 10/1996 | Sauer |
| 5,563,479 A | 10/1996 | Suzuki |
| 5,593,390 A | 1/1997 | Castellano |
| 5,609,580 A | 3/1997 | Kwiatkowski |
| 5,611,785 A | 3/1997 | Mito |
| 5,616,132 A | 4/1997 | Newman |
| 5,624,400 A | 4/1997 | Firth |
| 5,637,095 A | 6/1997 | Nason |
| 5,640,071 A | 6/1997 | Malaspina |
| 5,643,218 A | 7/1997 | Lynn |
| 5,645,530 A | 7/1997 | Boukhny |
| 5,645,955 A | 7/1997 | Maglica |
| 5,647,853 A | 7/1997 | Feldmann |
| 5,658,133 A | 8/1997 | Anderson |
| 5,658,256 A | 8/1997 | Shields |
| 5,661,372 A | 8/1997 | Ishimaru |
| 5,662,678 A | 9/1997 | Macklin |
| 5,672,160 A | 9/1997 | Oesterlind |
| D384,745 S | 10/1997 | Lattin |
| 5,683,367 A | 11/1997 | Jordan |
| 5,690,618 A | 11/1997 | Smith |
| 5,697,908 A | 12/1997 | Imbert |
| 5,697,916 A | 12/1997 | Schraga |
| 5,709,662 A | 1/1998 | Olive |
| 5,725,500 A | 3/1998 | Micheler |
| 5,728,075 A | 3/1998 | Levander |
| D393,314 S | 4/1998 | Meisner |
| 5,741,227 A | 4/1998 | Sealfon |
| 5,741,275 A | 4/1998 | Wyssmann |
| 5,766,186 A | 6/1998 | Faraz |
| 5,776,103 A | 7/1998 | Kriesel |
| 5,779,676 A | 7/1998 | Kriesel |
| 5,795,675 A | 8/1998 | Maglica |
| 5,800,420 A | 9/1998 | Gross |
| 5,807,375 A | 9/1998 | Gross |
| 5,810,167 A | 9/1998 | Fujii |
| 5,810,784 A | 9/1998 | Tamaro |
| 5,814,020 A | 9/1998 | Gross |
| 5,820,406 A | 10/1998 | Hetherington |
| 5,830,187 A | 11/1998 | Kriesel |
| 5,836,920 A | 11/1998 | Robertson |
| 5,839,537 A | 11/1998 | Nishino |
| 5,848,991 A | 12/1998 | Gross |
| 5,851,197 A | 12/1998 | Marano |
| 5,858,001 A | 1/1999 | Tsals |
| 5,858,008 A | 1/1999 | Capaccio |
| 5,868,710 A | 2/1999 | Battiato |
| 5,884,237 A | 3/1999 | Kanki |
| 5,893,842 A | 4/1999 | Imbert |
| 5,894,015 A | 4/1999 | Rechtin |
| 5,919,167 A | 7/1999 | Mulhauser |
| 5,925,018 A | 7/1999 | Ungerstedt |
| 5,926,596 A | 7/1999 | Edwards |
| 5,931,814 A | 8/1999 | Alex |
| 5,941,850 A | 8/1999 | Shah |
| 5,944,699 A | 8/1999 | Barrelle |
| 5,948,392 A | 9/1999 | Haslwanter |
| 5,954,697 A | 9/1999 | Srisathapat et al. |
| 5,957,895 A | 9/1999 | Sage |
| 5,968,011 A | 10/1999 | Larsen |
| 5,989,221 A | 11/1999 | Hjertman |
| 5,993,423 A | 11/1999 | Choi |
| 5,997,501 A | 12/1999 | Gross |
| 6,004,296 A | 12/1999 | Jansen |
| 6,004,297 A | 12/1999 | Steenfeldt-Jensen |
| 6,033,245 A | 3/2000 | Yamkovoy |
| 6,033,377 A | 3/2000 | Rasmussen |
| 6,039,713 A | 3/2000 | Botich |
| 6,045,533 A | 4/2000 | Kriesel |
| 6,064,797 A | 5/2000 | Crittendon |
| 6,074,369 A | 6/2000 | Sage |
| 6,081,098 A | 6/2000 | Bertness |
| 6,117,575 A | 9/2000 | Dinsdale |
| 6,138,865 A | 10/2000 | Gilmore |
| 6,139,399 A | 10/2000 | Deangelis |
| 6,149,614 A | 11/2000 | Dunshee |
| 6,160,487 A | 12/2000 | Deluca |
| 6,162,197 A | 12/2000 | Mohammad |
| 6,175,688 B1 | 1/2001 | Cassidy |
| 6,186,979 B1 | 2/2001 | Dysarz |
| 6,186,982 B1 | 2/2001 | Gross |
| 6,189,292 B1 | 2/2001 | Odell |
| 6,200,289 B1 | 3/2001 | Hochman |
| 6,200,296 B1 | 3/2001 | Dibiasi |
| 6,224,569 B1 | 5/2001 | Brimhall |
| 6,248,093 B1 | 6/2001 | Moberg |
| 6,270,478 B1 | 8/2001 | Morton |
| 6,270,481 B1 | 8/2001 | Mason |
| 6,277,095 B1 | 8/2001 | Kriesel |
| 6,277,098 B1 | 8/2001 | Klitmose |
| 6,277,099 B1 | 8/2001 | Strowe |
| 6,287,283 B1 | 9/2001 | Ljunggreen |
| 6,293,925 B1 | 9/2001 | Safabash |
| 6,302,633 B1 | 10/2001 | Poe |
| 6,305,908 B1 | 10/2001 | Hermann |
| 6,331,762 B1 | 12/2001 | Bertness |
| 6,336,729 B1 | 1/2002 | Pavelle |
| 6,345,968 B1 | 2/2002 | Shupe |
| 6,362,591 B1 | 3/2002 | Moberg |
| 6,377,848 B1 | 4/2002 | Garde |
| 6,391,005 B1 | 5/2002 | Lum |
| 6,423,029 B1 | 7/2002 | Elsberry |
| 6,423,035 B1 | 7/2002 | Das |
| 6,423,036 B1 | 7/2002 | Van Huizen |
| D461,243 S | 8/2002 | Niedospial, Jr. |
| D465,026 S | 10/2002 | May |
| 6,458,102 B1 | 10/2002 | Mann |
| 6,471,436 B1 | 10/2002 | Gjata |
| 6,485,461 B1 | 11/2002 | Mason |
| 6,485,465 B2 | 11/2002 | Moberg |
| 6,500,150 B1 | 12/2002 | Gross |
| 6,503,231 B1 | 1/2003 | Prausnitz |
| 6,511,336 B1 | 1/2003 | Turek |
| 6,517,517 B1 | 2/2003 | Farrugia |
| D471,274 S | 3/2003 | Diaz |
| D471,983 S | 3/2003 | Hippolyte |
| 6,530,901 B1 | 3/2003 | Tsukada |
| 6,554,800 B1 | 4/2003 | Nezhadian |
| 6,555,986 B2 | 4/2003 | Moberg |
| 6,558,351 B1 | 5/2003 | Steil |
| 6,558,365 B2 | 5/2003 | Zinger |
| 6,565,541 B2 | 5/2003 | Sharp |
| 6,585,695 B1 | 7/2003 | Adair et al. |
| 6,589,229 B1 | 7/2003 | Connelly |
| 6,595,205 B2 | 7/2003 | Andersson |
| 6,595,956 B1 | 7/2003 | Gross |
| 6,595,960 B2 | 7/2003 | West |
| 6,599,272 B1 | 7/2003 | Hjertman |
| 6,632,201 B1 | 10/2003 | Mathias |
| 6,645,181 B1 | 11/2003 | Lavi |
| 6,652,482 B2 | 11/2003 | Hochman |
| 6,656,158 B2 | 12/2003 | Mahoney |
| 6,656,159 B2 | 12/2003 | Flaherty |
| 6,659,980 B2 | 12/2003 | Moberg et al. |
| 6,673,033 B1 | 1/2004 | Sciulli |
| 6,679,862 B2 | 1/2004 | Diaz |
| 6,685,678 B2 | 2/2004 | Evans |

(56) References Cited

U.S. PATENT DOCUMENTS

| | | |
|---|---|---|
| 6,689,118 B2 | 2/2004 | Alchas |
| 6,699,218 B2 | 3/2004 | Flaherty |
| 6,719,141 B2 | 4/2004 | Heinz |
| 6,722,916 B2 | 4/2004 | Buccinna |
| 6,736,796 B2 | 5/2004 | Shekalim |
| 6,743,211 B1 | 6/2004 | Prausnitz |
| 6,749,587 B2 | 6/2004 | Flaherty |
| 6,752,783 B2 | 6/2004 | Hung |
| 6,752,787 B1 | 6/2004 | Causey, III |
| 6,767,336 B1 | 7/2004 | Kaplan |
| 6,768,425 B2 | 7/2004 | Flaherty |
| 6,786,890 B2 | 9/2004 | Preuthun et al. |
| 6,800,071 B1 | 10/2004 | McConnell et al. |
| 6,805,687 B2 | 10/2004 | Dextradeur |
| 6,817,990 B2 | 11/2004 | Yap et al. |
| 6,824,529 B2 | 11/2004 | Gross |
| 6,830,558 B2 | 12/2004 | Flaherty |
| 6,843,782 B2 | 1/2005 | Gross |
| 6,851,197 B2 | 2/2005 | Terry |
| 6,854,620 B2 | 2/2005 | Ramey |
| 6,905,298 B1 | 6/2005 | Haring |
| 6,907,679 B2 | 6/2005 | Yarborough |
| 6,908,452 B2 | 6/2005 | Diaz |
| 6,910,138 B2 | 6/2005 | Hayashi |
| 6,933,693 B2 | 8/2005 | Schuchmann |
| 6,943,531 B2 | 9/2005 | Fukaya |
| 6,950,028 B2 | 9/2005 | Zweig |
| 6,960,192 B1 | 11/2005 | Flaherty |
| 6,972,002 B2 | 12/2005 | Thorne |
| 6,979,316 B1 | 12/2005 | Rubin |
| 6,997,727 B1 | 2/2006 | Legrady |
| 7,001,360 B2 | 2/2006 | Veasey et al. |
| 7,004,104 B1 | 2/2006 | Kundus |
| 7,004,929 B2 | 2/2006 | McWethy |
| 7,025,226 B2 | 4/2006 | Ramey |
| 7,033,338 B2 | 4/2006 | Vilks |
| 7,034,223 B2 | 4/2006 | Fan |
| 7,048,715 B2 | 5/2006 | Diaz |
| 7,054,737 B2 | 5/2006 | Degner |
| 7,060,054 B2 | 6/2006 | Nissels |
| 7,060,059 B2 | 6/2006 | Keith |
| 7,063,684 B2 | 6/2006 | Moberg |
| 7,064,454 B2 | 6/2006 | Fukaya |
| 7,066,909 B1 | 6/2006 | Peter |
| 7,075,311 B1 | 7/2006 | Oshiro |
| 7,094,221 B2 | 8/2006 | Veasey |
| 7,097,637 B2 | 8/2006 | Triplett |
| 7,112,187 B2 | 9/2006 | Karlsson |
| 7,122,982 B2 | 10/2006 | Sasaya |
| 7,124,310 B2 | 10/2006 | Hayashi |
| 7,126,341 B2 | 10/2006 | Bertness |
| 7,127,288 B2 | 10/2006 | Sturman |
| 7,128,727 B2 | 10/2006 | Flaherty |
| 7,144,384 B2 | 12/2006 | Gorman |
| 7,193,521 B2 | 3/2007 | Moberg et al. |
| 7,214,209 B2 | 5/2007 | Mazzoni |
| D544,092 S | 6/2007 | Lewis |
| 7,225,694 B2 | 6/2007 | Said |
| 7,247,149 B2 | 7/2007 | Beyerlein |
| 7,247,150 B2 | 7/2007 | Bierman |
| 7,250,037 B2 | 7/2007 | Shermer |
| 7,267,669 B2 | 9/2007 | Staunton |
| RE39,923 E | 11/2007 | Blom |
| 7,291,132 B2 | 11/2007 | DeRuntz |
| 7,291,159 B2 | 11/2007 | Schmelzeisen-Redeker |
| 7,292,462 B2 | 11/2007 | Watanabe |
| 7,303,549 B2 | 12/2007 | Flaherty |
| 7,306,578 B2 | 12/2007 | Gray et al. |
| 7,326,194 B2 | 2/2008 | Zinger |
| 7,344,385 B2 | 3/2008 | Chen |
| 7,364,570 B2 | 4/2008 | Gerondale |
| 7,377,907 B2 | 5/2008 | Shekalim |
| 7,377,912 B2 | 5/2008 | Graf |
| 7,384,413 B2 | 6/2008 | Gross |
| 7,390,312 B2 | 6/2008 | Barrelle |
| 7,390,314 B2 | 6/2008 | Stutz, Jr. |
| 7,407,493 B2 | 8/2008 | Cane |
| 7,418,880 B1 | 9/2008 | Smith |
| D578,210 S | 10/2008 | Muta |
| 7,442,186 B2 | 10/2008 | Blomquist |
| 7,455,663 B2 | 11/2008 | Bikovsky |
| 7,459,571 B2 | 12/2008 | Schlitter |
| 7,465,290 B2 | 12/2008 | Reilly |
| 7,468,055 B2 | 12/2008 | Prais |
| 7,488,181 B2 | 2/2009 | Van Haaster |
| 7,497,842 B2 | 3/2009 | Diaz |
| 7,500,963 B2 | 3/2009 | Westbye |
| 7,501,587 B2 | 3/2009 | English |
| 7,503,786 B2 | 3/2009 | Kato |
| 7,524,304 B2 | 4/2009 | Genosar |
| 7,530,964 B2 | 5/2009 | Lavi |
| 7,540,858 B2 | 6/2009 | Dibiasi |
| 7,547,281 B2 | 6/2009 | Hayes |
| 7,563,253 B2 | 7/2009 | Tanner |
| 7,565,208 B2 | 7/2009 | Harris |
| 7,569,050 B2 | 8/2009 | Moberg |
| 7,579,716 B2 | 8/2009 | Sato |
| D600,341 S | 9/2009 | Loerwald |
| 7,585,287 B2 | 9/2009 | Bresina |
| 7,588,559 B2 | 9/2009 | Aravena |
| 7,589,974 B2 | 9/2009 | Grady |
| D602,155 S | 10/2009 | Foley |
| D602,586 S | 10/2009 | Foley |
| 7,597,682 B2 | 10/2009 | Moberg |
| D604,835 S | 11/2009 | Conley |
| 7,611,491 B2 | 11/2009 | Pickhard |
| 7,612,542 B2 | 11/2009 | Eguchi |
| 7,621,893 B2 | 11/2009 | Moberg et al. |
| 7,628,770 B2 | 12/2009 | Ethelfeld |
| 7,628,772 B2 | 12/2009 | McConnell et al. |
| 7,628,782 B2 | 12/2009 | Adair et al. |
| 7,637,891 B2 | 12/2009 | Wall |
| 7,637,899 B2 | 12/2009 | Woolston |
| 7,641,649 B2 | 1/2010 | Moberg |
| 7,642,787 B2 | 1/2010 | Bertness |
| 7,658,734 B2 | 2/2010 | Adair et al. |
| 7,660,627 B2 | 2/2010 | McNichols |
| 7,678,079 B2 | 3/2010 | Shermer |
| 7,682,338 B2 | 3/2010 | Griffin |
| 7,686,787 B2 | 3/2010 | Moberg |
| 7,690,456 B2 | 4/2010 | Deng |
| 7,692,399 B2 | 4/2010 | Harriman |
| 7,699,829 B2 | 4/2010 | Harris |
| 7,699,833 B2 | 4/2010 | Moberg |
| 7,704,088 B2 | 4/2010 | Sakamoto |
| 7,704,227 B2 | 4/2010 | Moberg |
| 7,704,229 B2 | 4/2010 | Moberg |
| 7,704,231 B2 | 4/2010 | Pongpairochana |
| 7,705,602 B2 | 4/2010 | Bertness |
| 7,708,717 B2 | 5/2010 | Estes |
| 7,713,238 B2 | 5/2010 | Mernoe |
| 7,713,240 B2 | 5/2010 | Istoc |
| 7,717,903 B2 | 5/2010 | Estes |
| 7,717,913 B2 | 5/2010 | Novak |
| 7,722,574 B2 | 5/2010 | Toman |
| 7,736,333 B2 | 6/2010 | Gillespie, III |
| 7,736,344 B2 | 6/2010 | Moberg |
| 7,740,600 B2 | 6/2010 | Slatkine |
| 7,744,589 B2 | 6/2010 | Mounce |
| 7,749,194 B2 | 7/2010 | Edwards |
| 7,753,879 B2 | 7/2010 | Mernoe |
| 7,758,548 B2 | 7/2010 | Gillespie |
| 7,758,550 B2 | 7/2010 | Bollenbach |
| 7,766,867 B2 | 8/2010 | Lynch |
| 7,766,873 B2 | 8/2010 | Moberg et al. |
| 7,776,030 B2 | 8/2010 | Estes |
| 7,780,636 B2 | 8/2010 | Radmer |
| 7,780,637 B2 | 8/2010 | Jerde |
| 7,789,857 B2 | 9/2010 | Moberg |
| 7,789,862 B2 | 9/2010 | Thorne, Jr. |
| 7,794,426 B2 | 9/2010 | Briones |
| 7,794,427 B2 | 9/2010 | Estes et al. |
| 7,801,599 B2 | 9/2010 | Young |
| 7,806,868 B2 | 10/2010 | De Polo et al. |

(56) References Cited

U.S. PATENT DOCUMENTS

| | | | |
|---|---|---|---|
| 7,815,622 | B2 | 10/2010 | Istoc |
| 7,828,528 | B2 | 11/2010 | Estes |
| 7,837,659 | B2 | 11/2010 | Bush, Jr. |
| 7,846,132 | B2 | 12/2010 | Gravesen |
| 7,854,723 | B2 | 12/2010 | Hwang |
| 7,857,131 | B2 | 12/2010 | Vedrine |
| 7,879,025 | B2 | 2/2011 | Jacobson |
| 7,879,026 | B2 | 2/2011 | Estes |
| 7,892,206 | B2 | 2/2011 | Moberg et al. |
| 7,901,382 | B2 | 3/2011 | Daily |
| 7,905,867 | B2 | 3/2011 | Veasey |
| 7,918,825 | B2 | 4/2011 | O'Connor |
| 7,918,843 | B2 | 4/2011 | Genosar |
| 7,935,104 | B2 | 5/2011 | Yodfat |
| 7,935,105 | B2 | 5/2011 | Miller |
| 7,938,803 | B2 | 5/2011 | Mernoe |
| 7,955,297 | B2 | 6/2011 | Radmer |
| 7,955,305 | B2 | 6/2011 | Moberg |
| 7,967,784 | B2 | 6/2011 | Pongpairochana |
| 7,967,795 | B1 | 6/2011 | Cabiri |
| 7,976,514 | B2 | 7/2011 | Abry |
| 7,981,105 | B2 | 7/2011 | Adair et al. |
| 7,988,683 | B2 | 8/2011 | Adair et al. |
| 7,993,300 | B2 | 8/2011 | Nyholm |
| 7,993,301 | B2 | 8/2011 | Boyd |
| 7,998,111 | B2 | 8/2011 | Moberg et al. |
| 7,998,116 | B2 | 8/2011 | Mernoe |
| 7,998,117 | B2 | 8/2011 | Gross |
| 7,998,131 | B2 | 8/2011 | Adair et al. |
| 8,002,752 | B2 | 8/2011 | Yodfat |
| 8,002,754 | B2 | 8/2011 | Kawamura |
| 8,008,892 | B2 | 8/2011 | Kikuchi |
| 8,021,357 | B2 | 9/2011 | Tanaka |
| 8,025,658 | B2 | 9/2011 | Chong |
| 8,029,459 | B2 | 10/2011 | Rush |
| 8,029,460 | B2 | 10/2011 | Rush |
| 8,029,469 | B2 | 10/2011 | Ethelfeld |
| 8,034,019 | B2 | 10/2011 | Nair |
| 8,034,026 | B2 | 10/2011 | Grant et al. |
| 8,038,648 | B2 | 10/2011 | Marksteiner |
| 8,038,666 | B2 | 10/2011 | Triplett |
| 8,057,431 | B2 | 11/2011 | Woehr |
| 8,057,436 | B2 | 11/2011 | Causey |
| 8,062,253 | B2 | 11/2011 | Nielsen |
| 8,062,255 | B2 | 11/2011 | Brunnberg |
| 8,062,257 | B2 | 11/2011 | Moberg et al. |
| 8,062,259 | B2 | 11/2011 | Nycz |
| 8,065,096 | B2 | 11/2011 | Moberg et al. |
| 8,066,694 | B2 | 11/2011 | Wagener |
| D650,079 | S | 12/2011 | Presta |
| D650,903 | S | 12/2011 | Kosinski |
| 8,086,306 | B2 | 12/2011 | Katzman |
| D652,503 | S | 1/2012 | Cameron, III |
| 8,105,279 | B2 | 1/2012 | Mernoe |
| 8,105,293 | B2 | 1/2012 | Pickhard |
| 8,114,046 | B2 | 2/2012 | Covino |
| 8,114,064 | B2 | 2/2012 | Alferness |
| 8,114,066 | B2 | 2/2012 | Naef |
| 8,118,781 | B2 | 2/2012 | Knopper et al. |
| 8,121,603 | B2 | 2/2012 | Zhi |
| D657,462 | S | 4/2012 | Siroky |
| 8,147,446 | B2 | 4/2012 | Yodfat |
| 8,151,169 | B2 | 4/2012 | Bieth |
| 8,152,764 | B2 | 4/2012 | Istoc |
| 8,152,770 | B2 | 4/2012 | Reid |
| 8,152,779 | B2 | 4/2012 | Cabiri |
| 8,152,793 | B2 | 4/2012 | Keinaenen et al. |
| 8,157,693 | B2 | 4/2012 | Waksmundzki |
| 8,157,769 | B2 | 4/2012 | Cabiri |
| 8,162,674 | B2 | 4/2012 | Cho |
| 8,162,923 | B2 | 4/2012 | Adams |
| 8,167,841 | B2 | 5/2012 | Teisen-Simony |
| 8,172,591 | B2 | 5/2012 | Wertz |
| 8,172,804 | B2 | 5/2012 | Bikovsky |
| 8,177,749 | B2 | 5/2012 | Slate |
| 8,182,447 | B2 | 5/2012 | Moberg et al. |
| 8,182,462 | B2 | 5/2012 | Istoc |
| 8,197,444 | B1 | 6/2012 | Bazargan |
| 8,206,296 | B2 | 6/2012 | Jennewine |
| 8,206,351 | B2 | 6/2012 | Sugimoto |
| 8,221,356 | B2 | 7/2012 | Enggaard |
| 8,221,359 | B2 | 7/2012 | Kristensen |
| 8,226,607 | B2 | 7/2012 | Carter |
| 8,226,608 | B2 | 7/2012 | Mernoe |
| 8,234,769 | B2 | 8/2012 | Leidig |
| 8,257,345 | B2 | 9/2012 | Adair et al. |
| 8,267,893 | B2 | 9/2012 | Moberg et al. |
| 8,267,921 | B2 | 9/2012 | Yodfat |
| 8,273,061 | B2 | 9/2012 | McConnell et al. |
| 8,287,520 | B2 | 10/2012 | Drew |
| 8,292,647 | B1 | 10/2012 | McGrath |
| 8,303,572 | B2 | 11/2012 | Adair et al. |
| 8,308,679 | B2 | 11/2012 | Hanson |
| 8,308,695 | B2 | 11/2012 | Laiosa |
| 8,323,250 | B2 | 12/2012 | Chong |
| 8,348,898 | B2 | 1/2013 | Cabiri |
| 8,361,028 | B2 | 1/2013 | Gross |
| 8,366,668 | B2 | 2/2013 | Maritan |
| 8,372,039 | B2 | 2/2013 | Mernoe |
| 8,373,421 | B2 | 2/2013 | Lindegger |
| 8,409,141 | B2 | 4/2013 | Johansen |
| 8,409,142 | B2 | 4/2013 | Causey |
| 8,409,143 | B2 | 4/2013 | Lanigan et al. |
| 8,409,149 | B2 | 4/2013 | Hommann |
| 8,414,533 | B2 | 4/2013 | Alexandersson |
| 8,414,557 | B2 | 4/2013 | Istoc |
| 8,425,468 | B2 | 4/2013 | Weston |
| 8,430,847 | B2 | 4/2013 | Mernoe |
| D685,083 | S | 6/2013 | Schneider |
| 8,465,455 | B2 | 6/2013 | Cabiri |
| 8,469,942 | B2 | 6/2013 | Kow |
| D687,141 | S | 7/2013 | Schneider |
| 8,474,332 | B2 | 7/2013 | Bente, IV |
| 8,475,408 | B2 | 7/2013 | Mernoe |
| 8,479,595 | B2 | 7/2013 | Vazquez |
| 8,483,980 | B2 | 7/2013 | Moberg et al. |
| 8,490,790 | B2 | 7/2013 | Cocheteux |
| 8,493,022 | B2 | 7/2013 | Bertness |
| 8,495,918 | B2 | 7/2013 | Bazargan |
| 8,496,862 | B2 | 7/2013 | Zelkovich |
| D687,536 | S | 8/2013 | Guarraia |
| 8,500,716 | B2 | 8/2013 | Adair et al. |
| 8,512,287 | B2 | 8/2013 | Cindrich |
| 8,512,295 | B2 | 8/2013 | Evans |
| 8,517,987 | B2 | 8/2013 | Istoc |
| 8,517,992 | B2 | 8/2013 | Jones |
| 8,523,803 | B1 | 9/2013 | Favreau |
| D692,552 | S | 10/2013 | Lovell |
| 8,551,046 | B2 | 10/2013 | Causey |
| 8,556,856 | B2 | 10/2013 | Bazargan |
| 8,562,364 | B2 | 10/2013 | Lin |
| 8,568,361 | B2 | 10/2013 | Yodfat et al. |
| 8,574,216 | B2 | 11/2013 | Istoc |
| 8,603,026 | B2 | 12/2013 | Favreau |
| 8,603,027 | B2 | 12/2013 | Favreau |
| 8,603,028 | B2 | 12/2013 | Mudd |
| 8,617,110 | B2 | 12/2013 | Moberg et al. |
| 8,622,966 | B2 | 1/2014 | Causey |
| 8,628,510 | B2 | 1/2014 | Bazargan |
| 8,632,499 | B2 | 1/2014 | Grant et al. |
| 8,647,074 | B2 | 2/2014 | Moberg et al. |
| 8,647,296 | B2 | 2/2014 | Moberg et al. |
| 8,647,303 | B2 | 2/2014 | Cowe |
| 8,668,672 | B2 | 3/2014 | Moberg et al. |
| 8,674,288 | B2 | 3/2014 | Hanson |
| 8,679,060 | B2 | 3/2014 | Mernoe |
| 8,679,062 | B2 | 3/2014 | Yodfat |
| 8,681,010 | B2 | 3/2014 | Moberg et al. |
| D702,834 | S | 4/2014 | Norton |
| 8,690,855 | B2 | 4/2014 | Alderete, Jr. |
| 8,708,961 | B2 | 4/2014 | Field |
| 8,715,237 | B2 | 5/2014 | Moberg et al. |
| 8,721,603 | B2 | 5/2014 | Lundquist |
| 8,751,237 | B2 | 6/2014 | Kubota |

(56) References Cited

U.S. PATENT DOCUMENTS

| | | |
|---|---|---|
| 8,753,326 B2 | 6/2014 | Chong |
| 8,753,331 B2 | 6/2014 | Murphy |
| 8,764,707 B2 | 7/2014 | Moberg |
| 8,764,723 B2 | 7/2014 | Chong |
| 8,771,222 B2 | 7/2014 | Kanderian, Jr. |
| 8,777,896 B2 | 7/2014 | Starkweather |
| 8,777,924 B2 | 7/2014 | Kanderian, Jr. |
| 8,777,925 B2 | 7/2014 | Patton |
| 8,784,369 B2 | 7/2014 | Starkweather |
| 8,784,370 B2 | 7/2014 | Lebel |
| 8,784,378 B2 | 7/2014 | Weinandy |
| 8,790,295 B1 | 7/2014 | Sigg |
| 8,795,224 B2 | 8/2014 | Starkweather |
| 8,795,231 B2 | 8/2014 | Chong |
| 8,795,260 B2 | 8/2014 | Drew |
| 8,801,668 B2 | 8/2014 | Ali |
| 8,801,679 B2 | 8/2014 | Iio |
| 8,808,230 B2 | 8/2014 | Rotstein |
| 8,808,269 B2 | 8/2014 | Bazargan |
| 8,810,394 B2 | 8/2014 | Kalpin |
| 8,814,379 B2 | 8/2014 | Griffiths |
| 8,845,587 B2 | 9/2014 | Lanigan et al. |
| 8,858,508 B2 | 10/2014 | Lavi |
| 8,864,739 B2 | 10/2014 | Moberg et al. |
| 8,870,818 B2 | 10/2014 | Alderete, Jr. |
| 8,876,770 B2 | 11/2014 | Kraft et al. |
| 8,876,778 B2 | 11/2014 | Carrel |
| 8,911,410 B2 | 12/2014 | Ekman |
| 8,915,882 B2 | 12/2014 | Cabiri |
| 8,915,886 B2 | 12/2014 | Cowe |
| 8,920,374 B2 | 12/2014 | Bokelman |
| 8,932,266 B2 | 1/2015 | Wozencroft |
| D723,157 S | 2/2015 | Clemente |
| 8,945,051 B2 | 2/2015 | Schriver |
| 8,979,802 B2 | 3/2015 | Woehr |
| 8,986,250 B2 | 3/2015 | Beebe |
| 8,992,475 B2 | 3/2015 | Mann |
| 9,011,164 B2 | 4/2015 | Filman |
| 9,011,371 B2 | 4/2015 | Moberg et al. |
| 9,011,387 B2 | 4/2015 | Ekman |
| 9,033,924 B2 | 5/2015 | Yavorsky |
| 9,033,925 B2 | 5/2015 | Moberg et al. |
| 9,050,406 B2 | 6/2015 | Kow |
| 9,061,104 B2 | 6/2015 | Daniel |
| 9,061,110 B2 | 6/2015 | Avery |
| 9,072,827 B2 | 7/2015 | Cabiri |
| 9,072,845 B2 | 7/2015 | Hiles |
| 9,089,475 B2 | 7/2015 | Fangrow |
| 9,089,641 B2 | 7/2015 | Kavazov |
| 9,107,999 B2 | 8/2015 | Moberg et al. |
| 9,138,534 B2 | 9/2015 | Yodfat |
| 9,149,575 B2 | 10/2015 | Cabiri |
| 9,173,996 B2 | 11/2015 | Gray et al. |
| 9,173,997 B2 | 11/2015 | Gross et al. |
| 9,180,248 B2 | 11/2015 | Moberg et al. |
| 9,205,188 B2 | 12/2015 | Lanigan et al. |
| 9,205,199 B2 | 12/2015 | Kemp |
| D747,799 S | 1/2016 | Norton |
| 9,233,215 B2 | 1/2016 | Hourmand |
| 9,242,044 B2 | 1/2016 | Markussen |
| 9,259,532 B2 | 2/2016 | Cabiri |
| 9,283,327 B2 | 3/2016 | Hourmand |
| 9,308,318 B2 | 4/2016 | Lanigan et al. |
| 9,308,327 B2 | 4/2016 | Marshall |
| 9,314,569 B2 | 4/2016 | Causey |
| 9,320,849 B2 | 4/2016 | Smith et al. |
| 9,327,073 B2 | 5/2016 | Moberg et al. |
| 9,339,607 B2 | 5/2016 | Angley et al. |
| 9,345,834 B2 | 5/2016 | Henley |
| 9,345,836 B2 | 5/2016 | Cabiri et al. |
| 9,350,634 B2 | 5/2016 | Fadell |
| 9,352,090 B2 | 5/2016 | Brereton |
| 9,364,606 B2 | 6/2016 | Cindrich |
| 9,364,608 B2 | 6/2016 | Moberg et al. |
| 9,381,300 B2 | 7/2016 | Smith |
| 9,393,365 B2 | 7/2016 | Cabiri |
| 9,393,369 B2 | 7/2016 | Cabiri |
| 9,421,321 B2 | 8/2016 | Hanson |
| 9,421,323 B2 | 8/2016 | Cabiri |
| 9,421,337 B2 | 8/2016 | Kemp |
| 9,427,531 B2 | 8/2016 | Hourmand |
| 9,433,732 B2 | 9/2016 | Moberg et al. |
| 9,433,733 B2 | 9/2016 | Moberg et al. |
| 9,446,188 B2 | 9/2016 | Grant et al. |
| 9,446,196 B2 | 9/2016 | Hourmand |
| 9,452,261 B2 | 9/2016 | Alon |
| D768,288 S | 10/2016 | O'Connor |
| 9,463,280 B2 | 10/2016 | Cabiri |
| 9,463,889 B2 | 10/2016 | Schmitz |
| 9,468,720 B2 | 10/2016 | Mudd |
| 9,474,859 B2 | 10/2016 | Ekman |
| 9,492,610 B2 | 11/2016 | Cabiri |
| 9,492,618 B2 | 11/2016 | Day |
| 9,492,622 B2 | 11/2016 | Brereton |
| D774,640 S | 12/2016 | Tyce |
| 9,511,190 B2 | 12/2016 | Cabiri |
| 9,522,234 B2 | 12/2016 | Cabiri |
| D776,262 S | 1/2017 | Tyce |
| D776,263 S | 1/2017 | Tyce |
| D776,264 S | 1/2017 | Tyce |
| D776,265 S | 1/2017 | Tyce |
| 9,539,384 B2 | 1/2017 | Servansky |
| 9,539,388 B2 | 1/2017 | Causey |
| 9,539,757 B2 | 1/2017 | Ramirez |
| 9,572,926 B2 | 2/2017 | Cabiri |
| 9,572,927 B2 | 2/2017 | Brüggemann et al. |
| 9,579,452 B2 | 2/2017 | Adair et al. |
| 9,579,471 B2 | 2/2017 | Carrel |
| 9,610,407 B2 | 4/2017 | Bruggemann et al. |
| 9,656,019 B2 | 5/2017 | Cabiri |
| 9,656,021 B2 | 5/2017 | Brereton |
| 9,656,025 B2 | 5/2017 | Boström |
| 9,707,335 B2 | 7/2017 | Agard |
| 9,707,356 B2 | 7/2017 | Hourmand |
| D794,776 S | 8/2017 | Tyce |
| 9,737,655 B2 | 8/2017 | Clemente |
| 9,744,306 B2 | 8/2017 | Cowe |
| 9,775,948 B2 | 10/2017 | Bechmann |
| 9,782,545 B2 | 10/2017 | Gross |
| 9,789,247 B2 | 10/2017 | Kamen et al. |
| 9,802,030 B2 | 10/2017 | Clemente |
| D804,019 S | 11/2017 | Costello |
| 9,814,830 B2 | 11/2017 | Mernoe |
| 9,814,832 B2 | 11/2017 | Agard |
| 9,814,839 B2 | 11/2017 | Eaton |
| D804,650 S | 12/2017 | Costello |
| D805,186 S | 12/2017 | Costello |
| D805,187 S | 12/2017 | Costello |
| D805,188 S | 12/2017 | Costello |
| D805,189 S | 12/2017 | Costello |
| D805,190 S | 12/2017 | Costello |
| 9,849,242 B2 | 12/2017 | Henley |
| 9,861,759 B2 | 1/2018 | Gross |
| 9,862,519 B2 | 1/2018 | Deutschle |
| D810,278 S | 2/2018 | Cabiri |
| D810,279 S | 2/2018 | Cabiri |
| D811,583 S | 2/2018 | Cabiri |
| D811,584 S | 2/2018 | Cabiri |
| D817,481 S | 5/2018 | Cabiri |
| 9,999,722 B2 | 6/2018 | Yodfat et al. |
| 10,010,681 B2 | 7/2018 | Koch et al. |
| 10,071,196 B2 | 9/2018 | Cabiri |
| 10,076,356 B2 | 9/2018 | Hadvary et al. |
| 10,143,794 B2 | 12/2018 | Lanigan et al. |
| 10,149,943 B2 | 12/2018 | Bar-El et al. |
| D838,367 S | 1/2019 | Norton |
| 10,166,335 B2 | 1/2019 | Reber |
| 10,207,048 B2 | 2/2019 | Gray et al. |
| 10,207,051 B2 | 2/2019 | Cereda |
| 10,227,161 B2 | 3/2019 | Auerbach |
| 10,232,116 B2 | 3/2019 | Ekman |
| 10,258,740 B2 | 4/2019 | McLoughlin et al. |
| D851,752 S | 6/2019 | Nazzaro |
| 10,376,641 B2 | 8/2019 | Hirschel |

(56) References Cited

U.S. PATENT DOCUMENTS

| | | |
|---|---|---|
| 10,376,647 B2 | 8/2019 | Farris et al. |
| 10,434,262 B2 | 10/2019 | Bendek |
| D865,945 S | 11/2019 | Nazzaro |
| 10,500,352 B2 | 12/2019 | Grant et al. |
| 10,561,798 B2 | 2/2020 | Holland et al. |
| 10,576,213 B2 | 3/2020 | Gylleby |
| 10,576,220 B2 | 3/2020 | Armes |
| 10,583,260 B2 | 3/2020 | Kemp |
| 10,603,430 B2 | 3/2020 | Shor et al. |
| 10,722,645 B2 | 7/2020 | Kamen et al. |
| 10,729,847 B2 | 8/2020 | Gray et al. |
| 10,758,679 B2 | 9/2020 | Bar-El et al. |
| 10,765,808 B2 | 9/2020 | Day |
| 10,842,942 B2 | 11/2020 | Ibuchi et al. |
| 11,027,059 B2 | 6/2021 | Niklaus et al. |
| 2001/0005781 A1 | 6/2001 | Bergens |
| 2001/0018937 A1 | 9/2001 | Nemoto |
| 2001/0025168 A1 | 9/2001 | Gross |
| 2001/0034502 A1 | 10/2001 | Moberg |
| 2001/0041869 A1 | 11/2001 | Causey |
| 2001/0056263 A1 | 12/2001 | Alchas |
| 2002/0010423 A1 | 1/2002 | Gross |
| 2002/0016569 A1 | 2/2002 | Critchlow |
| 2002/0022798 A1 | 2/2002 | Connelly |
| 2002/0026594 A1 | 2/2002 | Hayashi |
| 2002/0029018 A1 | 3/2002 | Jeffrey |
| 2002/0040208 A1 | 4/2002 | Flaherty |
| 2002/0043951 A1 | 4/2002 | Moberg |
| 2002/0045867 A1 | 4/2002 | Nielsen |
| 2002/0055711 A1 | 5/2002 | Lavi |
| 2002/0055718 A1 | 5/2002 | Hunt |
| 2002/0065488 A1 | 5/2002 | Suzuki |
| 2002/0100472 A1 | 8/2002 | Casper |
| 2002/0107487 A1 | 8/2002 | Preuthun |
| 2002/0120186 A1 | 8/2002 | Keimel |
| 2002/0123740 A1 | 9/2002 | Flaherty |
| 2002/0133114 A1 | 9/2002 | Itoh |
| 2002/0151855 A1 | 10/2002 | Douglas |
| 2002/0161332 A1 | 10/2002 | Ramey |
| 2002/0169215 A1 | 11/2002 | Meng |
| 2002/0173748 A1 | 11/2002 | McConnell et al. |
| 2002/0173769 A1 | 11/2002 | Gray et al. |
| 2003/0009133 A1 | 1/2003 | Ramey |
| 2003/0014018 A1 | 1/2003 | Giambattista |
| 2003/0038637 A1 | 2/2003 | Bertness |
| 2003/0050602 A1 | 3/2003 | Pettis |
| 2003/0060765 A1 | 3/2003 | Campbell |
| 2003/0069518 A1 | 4/2003 | Daley |
| 2003/0078195 A1 | 4/2003 | Kristensen |
| 2003/0109827 A1 | 6/2003 | Lavi |
| 2003/0125671 A1 | 7/2003 | Aramata |
| 2003/0130618 A1 | 7/2003 | Gray et al. |
| 2003/0135159 A1 | 7/2003 | Daily |
| 2003/0160683 A1 | 8/2003 | Blomquist |
| 2003/0167035 A1 | 9/2003 | Flaherty |
| 2003/0167039 A1 | 9/2003 | Moberg |
| 2003/0171717 A1 | 9/2003 | Farrugia |
| 2003/0181868 A1 | 9/2003 | Swenson |
| 2003/0199825 A1 | 10/2003 | Flaherty |
| 2003/0199827 A1 | 10/2003 | Thorne |
| 2003/0212370 A1 | 11/2003 | Barrelle |
| 2003/0216683 A1 | 11/2003 | Shekalim |
| 2003/0229308 A1 | 12/2003 | Tsals |
| 2003/0236498 A1 | 12/2003 | Gross |
| 2004/0000818 A1 | 1/2004 | Preuthun et al. |
| 2004/0002682 A1 | 1/2004 | Kovelman |
| 2004/0003493 A1 | 1/2004 | Adair et al. |
| 2004/0008009 A1 | 1/2004 | Fukaya |
| 2004/0010207 A1 | 1/2004 | Flaherty |
| 2004/0015131 A1 | 1/2004 | Flaherty |
| 2004/0030353 A1 | 2/2004 | Schmelzeisen-Redeker |
| 2004/0049160 A1 | 3/2004 | Hsieh |
| 2004/0049161 A1 | 3/2004 | Shearn |
| 2004/0064088 A1 | 4/2004 | Gorman |
| 2004/0082911 A1 | 4/2004 | Tiu |
| 2004/0085215 A1 | 5/2004 | Moberg |
| 2004/0092873 A1 | 5/2004 | Moberg |
| 2004/0116866 A1 | 6/2004 | Gorman |
| 2004/0122359 A1 | 6/2004 | Wenz |
| 2004/0122369 A1 | 6/2004 | Schriver |
| 2004/0127857 A1 | 7/2004 | Shemesh |
| 2004/0135078 A1 | 7/2004 | Mandro |
| 2004/0158172 A1 | 8/2004 | Hancock |
| 2004/0158205 A1 | 8/2004 | Savage |
| 2004/0171983 A1 | 9/2004 | Sparks |
| 2004/0186419 A1 | 9/2004 | Cho |
| 2004/0186424 A1 | 9/2004 | Hjertman |
| 2004/0186441 A1 | 9/2004 | Graf |
| 2004/0195989 A1 | 10/2004 | Harriman |
| 2004/0210196 A1 | 10/2004 | Bush, Jr. |
| 2004/0260233 A1 | 12/2004 | Garibotto |
| 2004/0267199 A1 | 12/2004 | Marshall |
| 2005/0027255 A1 | 2/2005 | Lavi |
| 2005/0033234 A1 | 2/2005 | Sadowski |
| 2005/0038388 A1 | 2/2005 | Hommann |
| 2005/0038391 A1 | 2/2005 | Wittland |
| 2005/0049553 A1 | 3/2005 | Triplett |
| 2005/0065466 A1 | 3/2005 | Vedrine |
| 2005/0065472 A1 | 3/2005 | Cindrich |
| 2005/0070845 A1 | 3/2005 | Faries |
| 2005/0071487 A1 | 3/2005 | Lu |
| 2005/0101912 A1 | 5/2005 | Faust |
| 2005/0113761 A1 | 5/2005 | Faust |
| 2005/0124940 A1 | 6/2005 | Martin |
| 2005/0135078 A1 | 6/2005 | Hamada |
| 2005/0154353 A1 | 7/2005 | Alheidt |
| 2005/0159706 A1 | 7/2005 | Wilkinson |
| 2005/0171476 A1 | 8/2005 | Judson |
| 2005/0171487 A1 | 8/2005 | Haury |
| 2005/0171512 A1 | 8/2005 | Flaherty |
| 2005/0174098 A1 | 8/2005 | Watanabe |
| 2005/0177136 A1 | 8/2005 | Miller |
| 2005/0189923 A1 | 9/2005 | Ohishi |
| 2005/0197626 A1 | 9/2005 | Moberg et al. |
| 2005/0197650 A1 | 9/2005 | Sugimoto |
| 2005/0201050 A1 | 9/2005 | Hayashi |
| 2005/0203461 A1 | 9/2005 | Flaherty |
| 2005/0209768 A1 | 9/2005 | Degner |
| 2005/0238507 A1 | 10/2005 | Diianni |
| 2005/0245956 A1 | 11/2005 | Steinemann |
| 2005/0258714 A1 | 11/2005 | Henderson |
| 2005/0283114 A1 | 12/2005 | Bresina |
| 2005/0288633 A1 | 12/2005 | Jeffrey |
| 2006/0013716 A1 | 1/2006 | Nason |
| 2006/0017412 A1 | 1/2006 | Sasaya |
| 2006/0030816 A1 | 2/2006 | Zubry |
| 2006/0036216 A1 | 2/2006 | Rimlinger |
| 2006/0095010 A1 | 5/2006 | Westbye |
| 2006/0095014 A1 | 5/2006 | Ethelfeld |
| 2006/0122577 A1 | 6/2006 | Poulsen |
| 2006/0124269 A1 | 6/2006 | Miyazaki |
| 2006/0173406 A1 | 8/2006 | Hayes |
| 2006/0173408 A1 | 8/2006 | Wyrick |
| 2006/0173410 A1 | 8/2006 | Moberg |
| 2006/0173439 A1 | 8/2006 | Thorne, Jr. |
| 2006/0184154 A1 | 8/2006 | Moberg |
| 2006/0195029 A1 | 8/2006 | Shults |
| 2006/0206054 A1 | 9/2006 | Shekalim |
| 2006/0206057 A1 | 9/2006 | Deruntz |
| 2006/0211982 A1 | 9/2006 | Prestrelski |
| 2006/0229569 A1 | 10/2006 | Lavi |
| 2006/0253086 A1 | 11/2006 | Moberg |
| 2006/0264831 A1 | 11/2006 | Skwarek |
| 2006/0264888 A1 | 11/2006 | Moberg |
| 2006/0264889 A1 | 11/2006 | Moberg |
| 2006/0264890 A1 | 11/2006 | Moberg |
| 2006/0264894 A1 | 11/2006 | Moberg |
| 2006/0270987 A1 | 11/2006 | Peter |
| 2006/0283465 A1 | 12/2006 | Nickel |
| 2006/0293722 A1 | 12/2006 | Slatkine |
| 2007/0016381 A1 | 1/2007 | Kamath |
| 2007/0021733 A1 | 1/2007 | Hansen |
| 2007/0025879 A1 | 2/2007 | Vandergaw |
| 2007/0049865 A1 | 3/2007 | Radmer |

(56) References Cited

U.S. PATENT DOCUMENTS

| | | |
|---|---|---|
| 2007/0073228 A1 | 3/2007 | Mernoe |
| 2007/0079894 A1 | 4/2007 | Kraus |
| 2007/0104596 A1 | 5/2007 | Preuthun |
| 2007/0106218 A1 | 5/2007 | Yodfat |
| 2007/0118405 A1 | 5/2007 | Campbell |
| 2007/0123819 A1 | 5/2007 | Mernoe |
| 2007/0129688 A1 | 6/2007 | Scheurer |
| 2007/0149926 A1 | 6/2007 | Moberg |
| 2007/0167912 A1 | 7/2007 | Causey |
| 2007/0179444 A1 | 8/2007 | Causey |
| 2007/0185449 A1 | 8/2007 | Mernoe |
| 2007/0191770 A1 | 8/2007 | Moberg |
| 2007/0197954 A1 | 8/2007 | Keenan |
| 2007/0197968 A1 | 8/2007 | Pongpairochana |
| 2007/0203454 A1 | 8/2007 | Shermer |
| 2007/0203528 A1 | 8/2007 | Vernon |
| 2007/0212103 A1 | 9/2007 | Kikuchi |
| 2007/0219480 A1 | 9/2007 | Kamen |
| 2007/0233003 A1 | 10/2007 | Radgowski |
| 2007/0233038 A1 | 10/2007 | Pruitt |
| 2007/0265568 A1 | 11/2007 | Tsals |
| 2007/0270745 A1 | 11/2007 | Nezhat |
| 2007/0274736 A1 | 11/2007 | Sato |
| 2007/0279011 A1 | 12/2007 | Jones |
| 2007/0282269 A1 | 12/2007 | Carter |
| 2008/0021439 A1 | 1/2008 | Brittingham |
| 2008/0033367 A1 | 2/2008 | Haury |
| 2008/0033369 A1 | 2/2008 | Kohlbrenner |
| 2008/0033393 A1 | 2/2008 | Edwards |
| 2008/0051710 A1 | 2/2008 | Moberg |
| 2008/0051711 A1 | 2/2008 | Mounce |
| 2008/0051727 A1 | 2/2008 | Moberg |
| 2008/0051730 A1 | 2/2008 | Bikovsky |
| 2008/0059133 A1 | 3/2008 | Edwards |
| 2008/0068870 A1 | 3/2008 | Eguchi |
| 2008/0097326 A1 | 4/2008 | Moberg |
| 2008/0097381 A1 | 4/2008 | Moberg |
| 2008/0097387 A1 | 4/2008 | Spector |
| 2008/0099015 A1 | 5/2008 | Pocock |
| 2008/0108951 A1 | 5/2008 | Jerde |
| 2008/0108953 A1 | 5/2008 | Moser |
| 2008/0125700 A1 | 5/2008 | Moberg |
| 2008/0140006 A1 | 6/2008 | Eskuri |
| 2008/0140014 A1 | 6/2008 | Miller |
| 2008/0140018 A1 | 6/2008 | Enggaard |
| 2008/0147004 A1 | 6/2008 | Mann |
| 2008/0156476 A1 | 7/2008 | Smisson |
| 2008/0167641 A1 | 7/2008 | Hansen |
| 2008/0188813 A1 | 8/2008 | Miller |
| 2008/0191556 A1 | 8/2008 | Hong |
| 2008/0195049 A1 | 8/2008 | Thalmann |
| 2008/0208138 A1 | 8/2008 | Lim |
| 2008/0215006 A1 | 9/2008 | Thorkild |
| 2008/0215013 A1 | 9/2008 | Felix-Faure |
| 2008/0215015 A1 | 9/2008 | Cindrich |
| 2008/0221522 A1 | 9/2008 | Moberg |
| 2008/0221523 A1 | 9/2008 | Moberg et al. |
| 2008/0234627 A1 | 9/2008 | Dent |
| 2008/0243087 A1 | 10/2008 | Enggaard |
| 2008/0249473 A1 | 10/2008 | Rutti |
| 2008/0255516 A1 | 10/2008 | Yodfat |
| 2008/0259666 A1 | 10/2008 | Eguchi |
| 2008/0262436 A1 | 10/2008 | Olson |
| 2008/0269687 A1 | 10/2008 | Chong |
| 2008/0269689 A1 | 10/2008 | Edwards |
| 2008/0269723 A1 | 10/2008 | Mastrototaro |
| 2008/0274630 A1 | 11/2008 | Shelton |
| 2008/0275407 A1 | 11/2008 | Scheurer |
| 2008/0275425 A1 | 11/2008 | Strickler |
| 2008/0281270 A1 | 11/2008 | Cross |
| 2008/0287873 A1 | 11/2008 | Liberatore |
| 2008/0294094 A1 | 11/2008 | Mhatre |
| 2008/0294143 A1 | 11/2008 | Tanaka |
| 2008/0306449 A1 | 12/2008 | Kristensen |
| 2008/0312601 A1 | 12/2008 | Cane |
| 2008/0315829 A1 | 12/2008 | Jones |
| 2008/0319383 A1 | 12/2008 | Byland |
| 2008/0319416 A1 | 12/2008 | Yodfat |
| 2009/0012478 A1 | 1/2009 | Weston |
| 2009/0041805 A1 | 2/2009 | Walker |
| 2009/0043245 A1 | 2/2009 | Nguyen |
| 2009/0043253 A1 | 2/2009 | Podaima |
| 2009/0048347 A1 | 2/2009 | Cohen |
| 2009/0048578 A1 | 2/2009 | Adams |
| 2009/0054750 A1 | 2/2009 | Jennewine |
| 2009/0054832 A1 | 2/2009 | Sugimoto |
| 2009/0054852 A1 | 2/2009 | Takano |
| 2009/0062767 A1 | 3/2009 | Van Antwerp |
| 2009/0069784 A1 | 3/2009 | Estes |
| 2009/0076360 A1 | 3/2009 | Brister |
| 2009/0076383 A1 | 3/2009 | Toews |
| 2009/0076453 A1 | 3/2009 | Mejlhede |
| 2009/0088694 A1 | 4/2009 | Carter |
| 2009/0088731 A1 | 4/2009 | Campbell |
| 2009/0093763 A1 | 4/2009 | Gonnelli |
| 2009/0093792 A1 | 4/2009 | Gross |
| 2009/0093793 A1 | 4/2009 | Gross |
| 2009/0099510 A1 | 4/2009 | Poulsen |
| 2009/0105650 A1 | 4/2009 | Wiegel |
| 2009/0105663 A1 | 4/2009 | Brand |
| 2009/0118662 A1 | 5/2009 | Schnall |
| 2009/0124977 A1 | 5/2009 | Jensen |
| 2009/0131860 A1 | 5/2009 | Nielsen |
| 2009/0139724 A1 | 6/2009 | Gray |
| 2009/0143730 A1 | 6/2009 | De Polo |
| 2009/0143735 A1 | 6/2009 | De Polo |
| 2009/0149830 A1 | 6/2009 | Spector |
| 2009/0182277 A1 | 7/2009 | Carter |
| 2009/0182284 A1 | 7/2009 | Morgan |
| 2009/0198215 A1 | 8/2009 | Chong |
| 2009/0204076 A1 | 8/2009 | Liversidge |
| 2009/0209896 A1 | 8/2009 | Selevan |
| 2009/0216103 A1 | 8/2009 | Brister |
| 2009/0234319 A1 | 9/2009 | Marksteiner |
| 2009/0240240 A1 | 9/2009 | Hines |
| 2009/0243234 A1 | 10/2009 | Sharifi |
| 2009/0253973 A1 | 10/2009 | Bashan |
| 2009/0254041 A1 | 10/2009 | Krag |
| 2009/0259176 A1 | 10/2009 | Yairi |
| 2009/0281585 A1 | 11/2009 | Katzman |
| 2009/0299288 A1 | 12/2009 | Sie |
| 2009/0299290 A1 | 12/2009 | Moberg |
| 2009/0299397 A1 | 12/2009 | Ruan |
| 2009/0326459 A1 | 12/2009 | Shipway et al. |
| 2009/0326509 A1 | 12/2009 | Muse |
| 2010/0010455 A1 | 1/2010 | Elahi |
| 2010/0018334 A1 | 1/2010 | Lessing |
| 2010/0019705 A1 | 1/2010 | Kimura |
| 2010/0030156 A1 | 2/2010 | Beebe |
| 2010/0030198 A1 | 2/2010 | Beebe |
| 2010/0037680 A1 | 2/2010 | Moberg |
| 2010/0044270 A1 | 2/2010 | Noble |
| 2010/0049128 A1 | 2/2010 | McKenzie |
| 2010/0049144 A1 | 2/2010 | McConnell |
| 2010/0057057 A1 | 3/2010 | Hayter |
| 2010/0076382 A1 | 3/2010 | Weston |
| 2010/0076412 A1 | 3/2010 | Rush |
| 2010/0081993 A1 | 4/2010 | O'Connor |
| 2010/0094255 A1 | 4/2010 | Nycz |
| 2010/0100076 A1 | 4/2010 | Rush |
| 2010/0100077 A1 | 4/2010 | Rush |
| 2010/0106098 A1 | 4/2010 | Atterbury |
| 2010/0121277 A1 | 5/2010 | Fehr |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat |
| 2010/0145305 A1 | 6/2010 | Alon |
| 2010/0152658 A1 | 6/2010 | Hanson |
| 2010/0160894 A1 | 6/2010 | Julian |
| 2010/0162548 A1 | 7/2010 | Leidig |
| 2010/0168607 A1 | 7/2010 | Miesel |
| 2010/0168683 A1 | 7/2010 | Cabiri |
| 2010/0185148 A1 | 7/2010 | Gillespie, III |

(56) References Cited

U.S. PATENT DOCUMENTS

| | | |
|---|---|---|
| 2010/0191187 A1 | 7/2010 | Kim |
| 2010/0198157 A1 | 8/2010 | Gyrn |
| 2010/0204657 A1 | 8/2010 | Yodfat |
| 2010/0211011 A1 | 8/2010 | Haar |
| 2010/0212407 A1 | 8/2010 | Stringham |
| 2010/0217192 A1 | 8/2010 | Moberg |
| 2010/0217193 A1 | 8/2010 | Moberg |
| 2010/0234767 A1 | 9/2010 | Sarstedt |
| 2010/0234805 A1 | 9/2010 | Kaufmann |
| 2010/0234830 A1 | 9/2010 | Straessler |
| 2010/0241065 A1 | 9/2010 | Moberg |
| 2010/0241103 A1 | 9/2010 | Kraft et al. |
| 2010/0253140 A1 | 10/2010 | Yamashita |
| 2010/0256486 A1 | 10/2010 | Savage |
| 2010/0262404 A1 | 10/2010 | Bertness |
| 2010/0264931 A1 | 10/2010 | Lindegger |
| 2010/0268169 A1 | 10/2010 | Llewellyn-Hyde |
| 2010/0274112 A1 | 10/2010 | Hoss |
| 2010/0274192 A1 | 10/2010 | Mernoe |
| 2010/0274202 A1 | 10/2010 | Hyde |
| 2010/0276411 A1 | 11/2010 | Hansen |
| 2010/0280499 A1 | 11/2010 | Yodfat |
| 2010/0286714 A1 | 11/2010 | Gyrn |
| 2010/0331826 A1 | 12/2010 | Field |
| 2011/0031805 A1 | 2/2011 | Yamashita |
| 2011/0034900 A1 | 2/2011 | Yodfat |
| 2011/0040280 A1 | 2/2011 | Ijitsu |
| 2011/0054399 A1 | 3/2011 | Chong |
| 2011/0054400 A1 | 3/2011 | Chong |
| 2011/0057510 A1 | 3/2011 | Yamashita |
| 2011/0060284 A1 | 3/2011 | Harr |
| 2011/0066131 A1 | 3/2011 | Cabiri |
| 2011/0092915 A1 | 4/2011 | Olson |
| 2011/0092952 A1 | 4/2011 | Voellmicke |
| 2011/0098887 A1 | 4/2011 | Fujimoto |
| 2011/0112504 A1 | 5/2011 | Causey |
| 2011/0119033 A1 | 5/2011 | Moberg |
| 2011/0125056 A1 | 5/2011 | Merchant |
| 2011/0137239 A1 | 6/2011 | Debelser |
| 2011/0137247 A1 | 6/2011 | Mesa |
| 2011/0144584 A1 | 6/2011 | Wozencroft |
| 2011/0152780 A1 | 6/2011 | Villette |
| 2011/0160654 A1 | 6/2011 | Hanson |
| 2011/0160655 A1 | 6/2011 | Hanson |
| 2011/0160666 A1 | 6/2011 | Hanson |
| 2011/0160669 A1 | 6/2011 | Gyrn |
| 2011/0166509 A1 | 7/2011 | Gross |
| 2011/0172645 A1 | 7/2011 | Moga |
| 2011/0172745 A1 | 7/2011 | Na |
| 2011/0178463 A1 | 7/2011 | Cabiri |
| 2011/0178472 A1 | 7/2011 | Cabiri |
| 2011/0184342 A1 | 7/2011 | Pesach |
| 2011/0201998 A1 | 8/2011 | Pongpairochana |
| 2011/0224614 A1 | 9/2011 | Moberg |
| 2011/0224616 A1 | 9/2011 | Slate |
| 2011/0224646 A1 | 9/2011 | Yodfat |
| 2011/0233393 A1 | 9/2011 | Hanson |
| 2011/0238031 A1 | 9/2011 | Adair |
| 2011/0245773 A1 | 10/2011 | Estes |
| 2011/0264326 A1 | 10/2011 | Iwasaki |
| 2011/0264383 A1 | 10/2011 | Moberg |
| 2011/0270160 A1 | 11/2011 | Mernoe |
| 2011/0272205 A1 | 11/2011 | Fujimoto |
| 2011/0273148 A1 | 11/2011 | Ueno |
| 2011/0282282 A1 | 11/2011 | Lorenzen |
| 2011/0282296 A1 | 11/2011 | Harms |
| 2011/0295205 A1 | 12/2011 | Kaufmann |
| 2011/0313238 A1 | 12/2011 | Reichenbach |
| 2011/0313351 A1 | 12/2011 | Kamen |
| 2011/0319861 A1 | 12/2011 | Wilk |
| 2011/0319919 A1 | 12/2011 | Curry |
| 2012/0004602 A1 | 1/2012 | Hanson |
| 2012/0004639 A1 | 1/2012 | Schoonmaker |
| 2012/0010594 A1 | 1/2012 | Holt |
| 2012/0022344 A1 | 1/2012 | Kube |
| 2012/0022496 A1 | 1/2012 | Causey |
| 2012/0022499 A1 | 1/2012 | Anderson |
| 2012/0025995 A1 | 2/2012 | Moberg |
| 2012/0029431 A1 | 2/2012 | Hwang |
| 2012/0035546 A1 | 2/2012 | Cabiri |
| 2012/0041364 A1 | 2/2012 | Smith |
| 2012/0041370 A1 | 2/2012 | Moberg |
| 2012/0041387 A1 | 2/2012 | Brüggemann et al. |
| 2012/0041414 A1 | 2/2012 | Estes |
| 2012/0059332 A1 | 3/2012 | Woehr |
| 2012/0071819 A1 | 3/2012 | Bruggemann |
| 2012/0071828 A1 | 3/2012 | Tojo |
| 2012/0078217 A1 | 3/2012 | Smith |
| 2012/0096953 A1 | 4/2012 | Bente, IV |
| 2012/0096954 A1 | 4/2012 | Vazquez |
| 2012/0101436 A1 | 4/2012 | Bazargan |
| 2012/0108933 A1 | 5/2012 | Liang |
| 2012/0109059 A1 | 5/2012 | Ranalletta |
| 2012/0116311 A1 | 5/2012 | Bruggemann |
| 2012/0118777 A1 | 5/2012 | Kakiuchi |
| 2012/0123387 A1 | 5/2012 | Gonzalez |
| 2012/0129362 A1 | 5/2012 | Hampo |
| 2012/0132203 A1 | 5/2012 | Hodson |
| 2012/0143136 A1 | 6/2012 | Constantineau |
| 2012/0160033 A1 | 6/2012 | Kow |
| 2012/0165733 A1 | 6/2012 | Bazargan |
| 2012/0165780 A1 | 6/2012 | Bazargan |
| 2012/0172804 A1 | 7/2012 | Plumptre |
| 2012/0172817 A1* | 7/2012 | Bruggemann .... A61M 5/14566 604/218 |
| 2012/0184917 A1 | 7/2012 | Bom |
| 2012/0192837 A1 | 8/2012 | Kitamura |
| 2012/0215169 A1 | 8/2012 | Moberg |
| 2012/0215199 A1 | 8/2012 | Moberg |
| 2012/0226234 A1 | 9/2012 | Bazargan |
| 2012/0227729 A1 | 9/2012 | Lundahl |
| 2012/0238961 A1 | 9/2012 | Julian |
| 2012/0259282 A1 | 10/2012 | Alderete, Jr. |
| 2012/0296174 A1 | 11/2012 | McCombie |
| 2012/0310153 A1 | 12/2012 | Moberg |
| 2012/0316506 A1 | 12/2012 | Sonderegger |
| 2013/0002045 A1 | 1/2013 | Hassan-Ali |
| 2013/0012873 A1 | 1/2013 | Gross |
| 2013/0012875 A1 | 1/2013 | Gross |
| 2013/0041346 A1 | 2/2013 | Alon |
| 2013/0060194 A1 | 3/2013 | Rotstein |
| 2013/0060233 A1 | 3/2013 | O'Connor |
| 2013/0068319 A1 | 3/2013 | Plumptre |
| 2013/0085457 A1 | 4/2013 | Schiff |
| 2013/0089992 A1 | 4/2013 | Yang |
| 2013/0096509 A1 | 4/2013 | Avery |
| 2013/0110049 A1 | 5/2013 | Cronenberg |
| 2013/0131589 A1 | 5/2013 | Mudd |
| 2013/0131604 A1 | 5/2013 | Avery |
| 2013/0133438 A1 | 5/2013 | Kow |
| 2013/0148270 A1 | 6/2013 | Fujioka |
| 2013/0172808 A1 | 7/2013 | Gilbert |
| 2013/0175192 A1 | 7/2013 | Iio et al. |
| 2013/0190691 A1 | 7/2013 | Cabiri |
| 2013/0190693 A1 | 7/2013 | Ekman |
| 2013/0200549 A1 | 8/2013 | Felts |
| 2013/0204187 A1 | 8/2013 | Avery |
| 2013/0204191 A1 | 8/2013 | Cindrich |
| 2013/0218089 A1 | 8/2013 | Davies |
| 2013/0218092 A1 | 8/2013 | Davies |
| 2013/0226098 A1 | 8/2013 | Tokumoto |
| 2013/0237953 A1 | 9/2013 | Kow |
| 2013/0245595 A1 | 9/2013 | Kow |
| 2013/0245596 A1 | 9/2013 | Cabiri |
| 2013/0245604 A1 | 9/2013 | Kouyoumjian |
| 2013/0253419 A1 | 9/2013 | Favreau |
| 2013/0253420 A1 | 9/2013 | Favreau |
| 2013/0253421 A1 | 9/2013 | Favreau |
| 2013/0253434 A1 | 9/2013 | Cabiri |
| 2013/0253472 A1 | 9/2013 | Cabiri |
| 2013/0267895 A1 | 10/2013 | Hemmingsen |
| 2013/0296785 A1 | 11/2013 | Cabiri |
| 2013/0296792 A1 | 11/2013 | Cabiri |
| 2013/0296799 A1 | 11/2013 | Degtiar |

(56) References Cited

U.S. PATENT DOCUMENTS

| | | |
|---|---|---|
| 2013/0296824 A1 | 11/2013 | Mo |
| 2013/0304021 A1 | 11/2013 | Cabiri et al. |
| 2013/0310753 A1 | 11/2013 | Oz |
| 2013/0310807 A1 | 11/2013 | Adair et al. |
| 2013/0323699 A1 | 12/2013 | Edwards |
| 2013/0331791 A1 | 12/2013 | Gross |
| 2013/0338584 A1 | 12/2013 | Mounce |
| 2014/0012229 A1 | 1/2014 | Bokelman |
| 2014/0018735 A1 | 1/2014 | Causey |
| 2014/0031747 A1 | 1/2014 | Ardehali |
| 2014/0052072 A1 | 2/2014 | Simas, Jr. |
| 2014/0055073 A1 | 2/2014 | Favreau |
| 2014/0055076 A1 | 2/2014 | Favreau |
| 2014/0058349 A1 | 2/2014 | Bazargan |
| 2014/0083517 A1 | 3/2014 | Moia |
| 2014/0088509 A1 | 3/2014 | Sonderegger |
| 2014/0094755 A1 | 4/2014 | Bazargan |
| 2014/0121633 A1 | 5/2014 | Causey |
| 2014/0128807 A1 | 5/2014 | Moberg |
| 2014/0128815 A1 | 5/2014 | Cabiri |
| 2014/0128835 A1 | 5/2014 | Moberg |
| 2014/0135692 A1 | 5/2014 | Alderete, Jr. |
| 2014/0135694 A1 | 5/2014 | Moberg |
| 2014/0142499 A1 | 5/2014 | Moberg |
| 2014/0148784 A1 | 5/2014 | Anderson |
| 2014/0148785 A1 | 5/2014 | Moberg |
| 2014/0163522 A1 | 6/2014 | Alderete, Jr. |
| 2014/0163526 A1 | 6/2014 | Cabiri |
| 2014/0171881 A1 | 6/2014 | Cabiri |
| 2014/0174223 A1 | 6/2014 | Gross |
| 2014/0188073 A1 | 7/2014 | Cabiri |
| 2014/0194819 A1 | 7/2014 | Maule |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0207080 A1 | 7/2014 | Allerdings |
| 2014/0207104 A1 | 7/2014 | Vouillamoz |
| 2014/0210631 A1 | 7/2014 | Zavis |
| 2014/0213975 A1 | 7/2014 | Clemente |
| 2014/0214001 A1 | 7/2014 | Mortazavi |
| 2014/0228768 A1 | 8/2014 | Eggert |
| 2014/0228780 A1 | 8/2014 | Cabiri |
| 2014/0236087 A1 | 8/2014 | Alderete, Jr. |
| 2014/0243786 A1 | 8/2014 | Gilbert |
| 2014/0249502 A1 | 9/2014 | Nie |
| 2014/0261758 A1 | 9/2014 | Wlodarczyk |
| 2014/0288511 A1 | 9/2014 | Tan-Malecki |
| 2014/0322935 A1 | 10/2014 | Filman |
| 2014/0330240 A1 | 11/2014 | Cabiri |
| 2014/0343406 A1 | 11/2014 | Damjanovic |
| 2014/0343503 A1 | 11/2014 | Holmqvist |
| 2014/0364808 A1 | 12/2014 | Niklaus et al. |
| 2015/0005703 A1 | 1/2015 | Hutchinson et al. |
| 2015/0011965 A1 | 1/2015 | Cabiri |
| 2015/0011976 A1 | 1/2015 | Vouillamoz |
| 2015/0032084 A1 | 1/2015 | Cabiri |
| 2015/0045729 A1 | 2/2015 | Denzer |
| 2015/0057613 A1 | 2/2015 | Clemente |
| 2015/0057615 A1 | 2/2015 | Mernoe |
| 2015/0073344 A1 | 3/2015 | Van Damme |
| 2015/0088071 A1 | 3/2015 | Cabiri |
| 2015/0112278 A1 | 4/2015 | Ray |
| 2015/0119797 A1 | 4/2015 | Cabiri |
| 2015/0119798 A1 | 4/2015 | Gross |
| 2015/0157806 A1 | 6/2015 | Knutsson |
| 2015/0165121 A1 | 6/2015 | Murakami |
| 2015/0174346 A1 | 6/2015 | Dhuppad |
| 2015/0180146 A1 | 6/2015 | Filman |
| 2015/0182691 A1 | 7/2015 | McLoughlin |
| 2015/0202375 A1 | 7/2015 | Schabbach |
| 2015/0224253 A1 | 8/2015 | Cabiri |
| 2015/0224258 A1 | 8/2015 | Holtwick |
| 2015/0250946 A1 | 9/2015 | Cabiri |
| 2015/0297833 A1 | 10/2015 | Henderson |
| 2015/0320990 A1 | 11/2015 | Burton |
| 2015/0367074 A1 | 12/2015 | Draper |
| 2015/0374926 A1 | 12/2015 | Gross |
| 2016/0015910 A1 | 1/2016 | Mukai |
| 2016/0030665 A1 | 2/2016 | Cabiri |
| 2016/0038691 A1 | 2/2016 | Mounce |
| 2016/0051756 A1 | 2/2016 | Cabiri |
| 2016/0051765 A1 | 2/2016 | Morris |
| 2016/0051767 A1 | 2/2016 | Higgins |
| 2016/0058941 A1 | 3/2016 | Wu |
| 2016/0136353 A1 | 5/2016 | Adams |
| 2016/0144117 A1 | 5/2016 | Chun |
| 2016/0151586 A1 | 6/2016 | Kemp |
| 2016/0158435 A1 | 6/2016 | Wu et al. |
| 2016/0158436 A1 | 6/2016 | Yang |
| 2016/0175515 A1 | 6/2016 | McCullough |
| 2016/0184512 A1 | 6/2016 | Marbet |
| 2016/0186906 A1* | 6/2016 | Blake ............... A61M 39/1011 285/319 |
| 2016/0193406 A1 | 7/2016 | Cabiri |
| 2016/0199590 A1 | 7/2016 | Schabbach |
| 2016/0199592 A1 | 7/2016 | Eggert |
| 2016/0213840 A1 | 7/2016 | Schabbach |
| 2016/0220755 A1 | 8/2016 | Lanigan et al. |
| 2016/0228644 A1 | 8/2016 | Cabiri |
| 2016/0228652 A1 | 8/2016 | Cabiri |
| 2016/0256352 A1 | 9/2016 | Bar-El |
| 2016/0296699 A1 | 10/2016 | Cabiri |
| 2016/0296713 A1 | 10/2016 | Schader |
| 2016/0296716 A1 | 10/2016 | Cabiri |
| 2016/0303324 A1 | 10/2016 | Cabiri |
| 2016/0317736 A1 | 11/2016 | Schabbach |
| 2016/0317737 A1 | 11/2016 | Schabbach |
| 2016/0331900 A1 | 11/2016 | Wei |
| 2016/0339168 A1 | 11/2016 | Hutchinson et al. |
| 2016/0346478 A1* | 12/2016 | Bar-El ............... A61M 5/31511 |
| 2016/0354553 A1 | 12/2016 | Anderson |
| 2017/0007774 A1 | 1/2017 | Brockmeier |
| 2017/0028132 A1 | 2/2017 | Cronenberg |
| 2017/0043092 A1 | 2/2017 | Murakami |
| 2017/0058349 A1 | 3/2017 | Levy |
| 2017/0080158 A1 | 3/2017 | Cabiri |
| 2017/0106138 A1 | 4/2017 | Cabiri |
| 2017/0175859 A1 | 6/2017 | Brockmeier |
| 2017/0224915 A1 | 8/2017 | Destefano |
| 2017/0246399 A1 | 8/2017 | Forlani |
| 2017/0246403 A1 | 8/2017 | Cowe |
| 2017/0281859 A1 | 10/2017 | Agard |
| 2017/0312450 A1 | 11/2017 | Gross |
| 2017/0354781 A1 | 12/2017 | Cronenberg |
| 2017/0354782 A1 | 12/2017 | Quinn |
| 2017/0354783 A1 | 12/2017 | Gazeley |
| 2017/0354785 A1 | 12/2017 | Gazeley |
| 2017/0354788 A1 | 12/2017 | Quinn |
| 2018/0001073 A1 | 1/2018 | Clemente |
| 2018/0008769 A1 | 1/2018 | O'Connor |
| 2018/0021508 A1 | 1/2018 | Destefano |
| 2018/0028747 A1 | 2/2018 | Hanson |
| 2018/0028765 A1 | 2/2018 | Waller et al. |
| 2018/0043091 A1 | 2/2018 | Agard |
| 2018/0055995 A1 | 3/2018 | Hanson |
| 2018/0133413 A1 | 5/2018 | Grant et al. |
| 2018/0214637 A1 | 8/2018 | Kemp |
| 2018/0221584 A1 | 8/2018 | Grimoldby |
| 2018/0236173 A1 | 8/2018 | McCaffrey |
| 2018/0304029 A1 | 10/2018 | Koch et al. |
| 2019/0015582 A1 | 1/2019 | Naftalovitz |
| 2019/0022306 A1 | 1/2019 | Gibson |
| 2019/0060578 A1 | 2/2019 | Farris et al. |
| 2019/0071217 A1 | 3/2019 | Brown |
| 2019/0091404 A1 | 3/2019 | Nazzaro |
| 2019/0099549 A1 | 4/2019 | Lanigan et al. |
| 2019/0117880 A1 | 4/2019 | Hirschel |
| 2019/0175821 A1 | 6/2019 | Kamen |
| 2019/0224415 A1 | 7/2019 | Dugand |
| 2019/0240417 A1 | 8/2019 | Hostettler |
| 2019/0328968 A1 | 10/2019 | Giambattista |
| 2019/0366012 A1 | 12/2019 | Gross |
| 2020/0009323 A1 | 1/2020 | Nair |

(56) References Cited

U.S. PATENT DOCUMENTS

| | | | |
|---|---|---|---|
| 2020/0164151 A1 | 5/2020 | Farris et al. | |
| 2020/0215270 A1 | 7/2020 | Ogawa et al. | |
| 2020/0282144 A1 | 9/2020 | Pearson | |
| 2020/0297929 A1 | 9/2020 | Zhang | |
| 2020/0360602 A1 | 11/2020 | Gray et al. | |
| 2021/0138157 A1 | 5/2021 | Bar-El | |
| 2021/0220551 A1 | 7/2021 | Dowd et al. | |

FOREIGN PATENT DOCUMENTS

| | | |
|---|---|---|
| CA | 2990453 A1 | 1/2017 |
| CN | 2107925 | 6/1992 |
| CN | 1224341 A | 7/1999 |
| CN | 1355716 | 6/2002 |
| CN | 1408443 A | 4/2003 |
| CN | 1505535 A | 6/2004 |
| CN | 1543363 | 11/2004 |
| CN | 1636605 A | 7/2005 |
| CN | 1658919 | 8/2005 |
| CN | 1671432 | 9/2005 |
| CN | 2748099 | 12/2005 |
| CN | 1747683 A | 3/2006 |
| CN | 1756573 A | 4/2006 |
| CN | 1863566 A | 11/2006 |
| CN | 1917912 | 2/2007 |
| CN | 1921900 | 2/2007 |
| CN | 1929884 A | 3/2007 |
| CN | 101001661 A | 7/2007 |
| CN | 101090749 A | 12/2007 |
| CN | 101163513 | 4/2008 |
| CN | 101227943 A | 7/2008 |
| CN | 101239205 A | 8/2008 |
| CN | 101267853 | 9/2008 |
| CN | 201233444 | 5/2009 |
| CN | 101448536 A | 6/2009 |
| CN | 101460207 A | 6/2009 |
| CN | 101478999 | 7/2009 |
| CN | 101522235 A | 9/2009 |
| CN | 101541362 A | 9/2009 |
| CN | 101557847 | 10/2009 |
| CN | 101573155 | 11/2009 |
| CN | 101641126 A | 2/2010 |
| CN | 101687083 A | 3/2010 |
| CN | 101703816 | 5/2010 |
| CN | 101868269 | 10/2010 |
| CN | 101868273 A | 10/2010 |
| CN | 201692438 U | 1/2011 |
| CN | 101970033 A | 2/2011 |
| CN | 102022308 A | 4/2011 |
| CN | 102038998 | 5/2011 |
| CN | 102083483 | 6/2011 |
| CN | 102083487 | 6/2011 |
| CN | 102089024 | 6/2011 |
| CN | 201941304 U | 8/2011 |
| CN | 102186733 A | 9/2011 |
| CN | 102245228 | 11/2011 |
| CN | 102245235 | 11/2011 |
| CN | 102256657 A | 11/2011 |
| CN | 202086877 | 12/2011 |
| CN | 102307606 | 1/2012 |
| CN | 102370487 | 3/2012 |
| CN | 102378638 A | 3/2012 |
| CN | 102480215 | 5/2012 |
| CN | 102573616 | 7/2012 |
| CN | 102639169 A | 8/2012 |
| CN | 102639174 | 8/2012 |
| CN | 102665805 A | 9/2012 |
| CN | 102733161 | 10/2012 |
| CN | 102883759 | 1/2013 |
| CN | 102917739 | 2/2013 |
| CN | 102958550 | 3/2013 |
| CN | 102971027 | 3/2013 |
| CN | 103079616 A | 5/2013 |
| CN | 1033118737 | 5/2013 |
| CN | 103269736 | 8/2013 |
| CN | 103520792 | 1/2014 |
| CN | 104127938 | 11/2014 |
| CN | 104132038 A | 11/2014 |
| CN | 104219998 | 12/2014 |
| CN | 104245018 | 12/2014 |
| CN | 104321092 | 1/2015 |
| CN | 104321093 | 1/2015 |
| CN | 104321100 | 1/2015 |
| CN | 104334216 | 2/2015 |
| CN | 104379196 | 2/2015 |
| CN | 104394912 | 3/2015 |
| CN | 1047033641 A | 6/2015 |
| CN | 104759006 | 7/2015 |
| CN | 104812428 | 7/2015 |
| CN | 104853787 | 8/2015 |
| CN | 104955504 A | 9/2015 |
| CN | 105025958 | 11/2015 |
| CN | 105102025 A | 11/2015 |
| CN | 105107065 | 12/2015 |
| CN | 105307709 | 2/2016 |
| CN | 105324140 | 2/2016 |
| CN | 105816942 | 8/2016 |
| CN | 205434562 | 8/2016 |
| CN | 105979990 | 9/2016 |
| CN | 106178185 | 12/2016 |
| CN | 106714878 | 5/2017 |
| DE | 855313 C | 11/1952 |
| DE | 1064693 B | 9/1959 |
| DE | 19518807 A1 | 12/1995 |
| DE | 19717107 A1 | 11/1998 |
| EP | 0017412 A1 | 10/1980 |
| EP | 0222656 A1 | 5/1987 |
| EP | 0401179 A1 | 12/1990 |
| EP | 0526986 A1 | 2/1993 |
| EP | 0744975 A1 | 12/1996 |
| EP | 0851774 A1 | 7/1998 |
| EP | 0925082 A1 | 6/1999 |
| EP | 1003581 A1 | 5/2000 |
| EP | 1003581 B1 | 11/2000 |
| EP | 1124600 A1 | 8/2001 |
| EP | 1156843 | 11/2001 |
| EP | 1219312 A2 | 7/2002 |
| EP | 1249250 A1 | 10/2002 |
| EP | 1472477 A1 | 11/2004 |
| EP | 1530979 A1 | 5/2005 |
| EP | 1666080 A1 | 6/2006 |
| EP | 1372762 B1 | 2/2007 |
| EP | 1930038 A2 | 6/2008 |
| EP | 1974759 A1 | 10/2008 |
| EP | 2060606 A1 | 5/2009 |
| EP | 2140897 A1 | 1/2010 |
| EP | 2173413 A1 | 4/2010 |
| EP | 2185227 A2 | 5/2010 |
| EP | 2192935 A1 | 6/2010 |
| EP | 1624913 B1 | 7/2010 |
| EP | 2316510 A2 | 5/2011 |
| EP | 2345441 A1 | 7/2011 |
| EP | 2361648 A1 | 8/2011 |
| EP | 2364739 A1 | 9/2011 |
| EP | 2364741 A1 | 9/2011 |
| EP | 2393534 A1 | 12/2011 |
| EP | 2412395 A1 | 2/2012 |
| EP | 2452708 A1 | 5/2012 |
| EP | 2468340 A1 | 6/2012 |
| EP | 2468342 A1 | 6/2012 |
| EP | 2498589 A1 | 9/2012 |
| EP | 2574355 A1 | 4/2013 |
| EP | 2578188 A1 | 4/2013 |
| EP | 2650031 A1 | 10/2013 |
| EP | 2698180 A1 | 2/2014 |
| EP | 2712650 A1 | 4/2014 |
| EP | 2714155 A2 | 4/2014 |
| EP | 2727617 A1 | 5/2014 |
| EP | 2799740 A2 | 11/2014 |
| EP | 2393535 B1 | 3/2015 |
| EP | 2862588 A1 | 4/2015 |
| EP | 2878321 A1 | 6/2015 |
| EP | 2886144 A1 | 6/2015 |
| EP | 2454483 B1 | 8/2015 |

(56) References Cited

FOREIGN PATENT DOCUMENTS

| | | |
|---|---|---|
| EP | 2932993 A1 | 10/2015 |
| EP | 1904130 B1 | 3/2016 |
| EP | 2991705 A1 | 3/2016 |
| EP | 3124066 | 2/2017 |
| EP | 3125066 | 2/2017 |
| EP | 3266478 A1 | 1/2018 |
| EP | 2819724 B1 | 3/2019 |
| EP | 3266478 B1 | 1/2020 |
| FR | 2770136 A1 | 4/1999 |
| FR | 2905273 A1 | 3/2008 |
| GB | 2436526 A | 10/2007 |
| JP | S55146165 | 11/1980 |
| JP | S62112566 A | 5/1987 |
| JP | S63287364 | 11/1988 |
| JP | H01172843 U | 12/1989 |
| JP | H05062828 A | 3/1993 |
| JP | H07194701 A | 8/1995 |
| JP | 3035448 U | 3/1997 |
| JP | H09505758 A | 6/1997 |
| JP | H10167593 | 6/1998 |
| JP | H11507260 A | 6/1999 |
| JP | 2000107289 A | 4/2000 |
| JP | 2000515394 A | 11/2000 |
| JP | 2001512992 A | 8/2001 |
| JP | 2002505601 A | 2/2002 |
| JP | 2002507459 A | 3/2002 |
| JP | 2002528234 | 9/2002 |
| JP | 2002528676 A | 9/2002 |
| JP | 2003501157 A | 1/2003 |
| JP | 2003527138 A | 9/2003 |
| JP | 2003534061 A | 11/2003 |
| JP | 2004501721 A | 1/2004 |
| JP | 2004512100 A | 4/2004 |
| JP | 2005523127 A | 8/2005 |
| JP | 2005527249 A | 9/2005 |
| JP | 2005270629 A | 10/2005 |
| JP | 2006501043 | 1/2006 |
| JP | 2006507067 A | 3/2006 |
| JP | 2006510450 A | 3/2006 |
| JP | 2006525046 A | 11/2006 |
| JP | 2007509661 A | 4/2007 |
| JP | 2007306990 A | 11/2007 |
| JP | 2008100762 A | 5/2008 |
| JP | 2008534131 A | 8/2008 |
| JP | 2008220961 A | 9/2008 |
| JP | 2009020101 | 1/2009 |
| JP | 2009502273 A | 1/2009 |
| JP | 2009101093 A | 5/2009 |
| JP | 4305704 B2 | 7/2009 |
| JP | 2010501281 A | 1/2010 |
| JP | 2010540054 A | 12/2010 |
| JP | 2010540156 A | 12/2010 |
| JP | 2011136153 A | 7/2011 |
| JP | 2012010954 | 1/2012 |
| JP | 2012100927 A | 5/2012 |
| JP | 4947871 B2 | 6/2012 |
| JP | 2012516738 | 7/2012 |
| JP | 2013500811 A | 1/2013 |
| JP | 2013504405 | 2/2013 |
| JP | 2013505433 A | 2/2013 |
| JP | 2013517094 | 5/2013 |
| JP | 2013517095 A | 5/2013 |
| JP | 2013519473 A | 5/2013 |
| JP | 2013521084 A | 6/2013 |
| JP | 2013523292 | 6/2013 |
| JP | 2013524905 | 6/2013 |
| JP | 2013524906 | 6/2013 |
| JP | 2013524907 | 6/2013 |
| JP | 2013530778 A | 8/2013 |
| JP | 2013531520 A | 8/2013 |
| JP | 2013531540 A | 8/2013 |
| JP | 2014010954 | 1/2014 |
| JP | 2014030489 A | 2/2014 |
| JP | 2014515669 A | 7/2014 |
| JP | 2014518743 A | 8/2014 |
| JP | 2014521443 A | 8/2014 |
| JP | 2014525339 A | 9/2014 |
| JP | 5616906 B2 | 10/2014 |
| JP | 2015514486 A | 5/2015 |
| JP | 2015144850 | 8/2015 |
| JP | 2015524722 A | 8/2015 |
| JP | 2015166048 | 9/2015 |
| JP | 2015536162 A | 12/2015 |
| JP | 2015536715 A | 12/2015 |
| JP | 2016525428 A | 8/2016 |
| JP | 2016530016 A | 9/2016 |
| JP | 2017200617 | 11/2017 |
| KR | 20140000766 U | 2/2014 |
| WO | 8911302 A1 | 11/1989 |
| WO | 9009202 A1 | 8/1990 |
| WO | 9307922 A1 | 4/1993 |
| WO | 9321974 | 11/1993 |
| WO | 9407553 A1 | 4/1994 |
| WO | 94/15660 A1 | 7/1994 |
| WO | 1994015660 A1 | 7/1994 |
| WO | 9513838 A1 | 5/1995 |
| WO | 9521645 A1 | 8/1995 |
| WO | 9609083 A1 | 3/1996 |
| WO | 9632975 A1 | 10/1996 |
| WO | 97/00091 A1 | 1/1997 |
| WO | 9710012 A1 | 3/1997 |
| WO | 9721457 A1 | 6/1997 |
| WO | 9733638 A1 | 9/1997 |
| WO | 9857683 A1 | 12/1998 |
| WO | 9857686 A1 | 12/1998 |
| WO | 9929151 A1 | 6/1999 |
| WO | 9959665 A1 | 11/1999 |
| WO | 00/25844 A1 | 5/2000 |
| WO | 0069509 A1 | 11/2000 |
| WO | 0130415 A2 | 5/2001 |
| WO | 0130421 A2 | 5/2001 |
| WO | 0170304 A1 | 9/2001 |
| WO | 0172357 A2 | 10/2001 |
| WO | 0187384 A1 | 11/2001 |
| WO | 0189607 A2 | 11/2001 |
| WO | 0189613 A1 | 11/2001 |
| WO | 0202165 A2 | 1/2002 |
| WO | 0204049 A1 | 1/2002 |
| WO | 0234315 A1 | 5/2002 |
| WO | 0238204 A2 | 5/2002 |
| WO | 02056934 A2 | 7/2002 |
| WO | 02056943 A2 | 7/2002 |
| WO | 02072182 A1 | 9/2002 |
| WO | 03026726 | 4/2003 |
| WO | 03062672 A1 | 7/2003 |
| WO | 03090833 A1 | 11/2003 |
| WO | 03103750 A1 | 12/2003 |
| WO | 2004000397 A1 | 12/2003 |
| WO | 2004032989 A2 | 4/2004 |
| WO | 2004032990 A2 | 4/2004 |
| WO | 2004069302 A2 | 8/2004 |
| WO | 2004098684 A2 | 11/2004 |
| WO | 2004105841 A1 | 12/2004 |
| WO | 2005018703 A2 | 3/2005 |
| WO | 2005028358 | 3/2005 |
| WO | 2005037350 A2 | 4/2005 |
| WO | 2005070485 A1 | 8/2005 |
| WO | 2005072795 A2 | 8/2005 |
| WO | 2005077441 A2 | 8/2005 |
| WO | 2006016364 A2 | 2/2006 |
| WO | 2006018617 A1 | 2/2006 |
| WO | 2006037434 A1 | 4/2006 |
| WO | 2006052737 A1 | 5/2006 |
| WO | 2006069380 A1 | 6/2006 |
| WO | 2006102676 A1 | 9/2006 |
| WO | 2006104806 A2 | 10/2006 |
| WO | 2006121921 A2 | 11/2006 |
| WO | 2006127905 | 11/2006 |
| WO | 2007017052 A1 | 2/2007 |
| WO | 2007051563 A1 | 5/2007 |
| WO | 2007056504 A1 | 5/2007 |
| WO | 2007066152 A2 | 6/2007 |
| WO | 2007073228 A1 | 6/2007 |
| WO | 2007092618 A2 | 8/2007 |

(56) References Cited

FOREIGN PATENT DOCUMENTS

| | | |
|---|---|---|
| WO | 2007/119178 A2 | 10/2007 |
| WO | 2007130868 A1 | 11/2007 |
| WO | 2008001377 A2 | 1/2008 |
| WO | 2008014908 A1 | 2/2008 |
| WO | 2008024781 | 2/2008 |
| WO | 2008024810 A2 | 2/2008 |
| WO | 2008024814 A2 | 2/2008 |
| WO | 2008034743 A1 | 3/2008 |
| WO | 2008057976 A2 | 5/2008 |
| WO | 2008072229 A2 | 6/2008 |
| WO | 2008076459 A1 | 6/2008 |
| WO | 2008078318 A2 | 7/2008 |
| WO | 2008129549 A1 | 10/2008 |
| WO | 2008131684 | 11/2008 |
| WO | 2009019438 A1 | 2/2009 |
| WO | 2009022132 A2 | 2/2009 |
| WO | 2009/043564 A1 | 4/2009 |
| WO | 2009043000 A1 | 4/2009 |
| WO | 2009044401 A2 | 4/2009 |
| WO | 2009046989 A2 | 4/2009 |
| WO | 2009/069064 A1 | 6/2009 |
| WO | 2009081262 A1 | 7/2009 |
| WO | 2009125398 A2 | 10/2009 |
| WO | 2009144085 A2 | 12/2009 |
| WO | 2010078227 A1 | 7/2010 |
| WO | 2010078242 A1 | 7/2010 |
| WO | 2010089313 A1 | 8/2010 |
| WO | 2010117841 | 10/2010 |
| WO | 2011034799 A1 | 3/2011 |
| WO | 2011075105 A1 | 6/2011 |
| WO | 2011090955 A1 | 7/2011 |
| WO | 2011090956 A2 | 7/2011 |
| WO | 2011091265 | 7/2011 |
| WO | 2011097487 | 8/2011 |
| WO | 2011101378 A1 | 8/2011 |
| WO | 2011104711 A1 | 9/2011 |
| WO | 2011110872 A1 | 9/2011 |
| WO | 2011113806 A1 | 9/2011 |
| WO | 2011124631 A1 | 10/2011 |
| WO | 2011129175 A1 | 10/2011 |
| WO | 2011131778 A1 | 10/2011 |
| WO | 2011131780 A2 | 10/2011 |
| WO | 2011131781 A1 | 10/2011 |
| WO | 2011133823 A1 | 10/2011 |
| WO | 2011141907 A1 | 11/2011 |
| WO | 2011156373 A1 | 12/2011 |
| WO | 2012000836 A1 | 1/2012 |
| WO | 2012003221 A1 | 1/2012 |
| WO | 2012032411 A2 | 3/2012 |
| WO | 2012040528 A1 | 3/2012 |
| WO | 2012064258 A1 | 5/2012 |
| WO | 2012108955 | 8/2012 |
| WO | 2012134588 A1 | 10/2012 |
| WO | 2012145685 A1 | 10/2012 |
| WO | 2012145752 A2 | 10/2012 |
| WO | 2012160157 A1 | 11/2012 |
| WO | 2012160160 A1 | 11/2012 |
| WO | 2012160164 | 11/2012 |
| WO | 2012164397 A1 | 12/2012 |
| WO | 2012168691 A1 | 12/2012 |
| WO | 2013036602 A1 | 3/2013 |
| WO | 2013058697 A1 | 4/2013 |
| WO | 2013115843 A1 | 8/2013 |
| WO | 2013148270 A2 | 10/2013 |
| WO | 2013148435 A1 | 10/2013 |
| WO | 2013173092 A1 | 11/2013 |
| WO | 2014039574 | 3/2014 |
| WO | 2014052676 A1 | 4/2014 |
| WO | 2014060563 A2 | 4/2014 |
| WO | 2014070453 A1 | 5/2014 |
| WO | 2014081411 A1 | 5/2014 |
| WO | 2014107408 A1 | 7/2014 |
| WO | 2014132293 A1 | 9/2014 |
| WO | 2014144096 | 9/2014 |
| WO | 2014159017 A1 | 10/2014 |
| WO | 2014179117 A1 | 11/2014 |
| WO | 2014179210 A1 | 11/2014 |
| WO | 2014179774 A1 | 11/2014 |
| WO | 2014194183 A2 | 12/2014 |
| WO | 2015018787 A1 | 2/2015 |
| WO | 2015048791 A1 | 4/2015 |
| WO | 2015048803 A2 | 4/2015 |
| WO | 2015078868 A1 | 6/2015 |
| WO | 2015091758 A1 | 6/2015 |
| WO | 2015091850 A1 | 6/2015 |
| WO | 2015114158 A1 | 8/2015 |
| WO | 2015114428 A1 | 8/2015 |
| WO | 2015118358 A1 | 8/2015 |
| WO | 2015146276 | 10/2015 |
| WO | 2015163009 A1 | 10/2015 |
| WO | 2015187797 | 12/2015 |
| WO | 2016060986 | 4/2016 |
| WO | 2016087626 A1 | 6/2016 |
| WO | 2016087627 A1 | 6/2016 |
| WO | 2016141082 A1 | 9/2016 |
| WO | 2016196934 | 12/2016 |
| WO | 2017022639 A1 | 2/2017 |
| WO | 2017033193 | 3/2017 |
| WO | 2017041996 A1 | 3/2017 |
| WO | 2017064483 | 4/2017 |
| WO | 2017161076 A1 | 9/2017 |
| WO | 2017210448 | 12/2017 |
| WO | 2018060023 | 4/2018 |
| WO | 2018222521 A1 | 12/2018 |
| WO | 2019224782 A1 | 11/2019 |
| WO | 2020120087 A1 | 6/2020 |
| WO | 2020193468 A1 | 10/2020 |

OTHER PUBLICATIONS

Int'l Preliminary Report on Patentability dated Dec. 3, 2019 in Int'l Applicaiton No. PCT/US2018/034597.
Int'l Search Report and Written Opinion dated Aug. 7, 2018 in Int'l Application No. PCT/US2018/034597.
Office Action dated Dec. 15, 2020 in Japanese Application No. 2019-566118.
Office Action dated Jul. 1, 2016 in U.S. Appl. No. 15/132,740 by Cabiri.
Office Action dated Jul. 2, 2015 in U.S. Appl. No. 14/096,977 by Cabiri.
Office Action dated Jul. 8, 2016 in CN Application No. 201510695320.8.
Office Action dated Jul. 9, 2020 in EP Application No. 16828833.0.
Office Action dated May 4, 2016 in U.S. Appl. No. 15/069,080 by Cabiri.
Office Action dated Oct. 5, 2016 in U.S. Appl. No. 13/964,651, by Gross.
Office Action dated Sep. 27, 2020 in CN Application No. 201680088261.0.
Office Action dated Sep. 29, 2020 in JP Application No. 2019-505206.
Search Report dated Nov. 24, 2015 in EP Application No. 14166592.7.
Search Report dated Oct. 14, 2016 in CN Application No. 2014101783742.
U.S. Appl. No. 60/997,459, filed Oct. 2, 2007.
U.S. Appl. No. 61/192,198, filed Sep. 15, 2008.
Office Action dated Apr. 23, 2015 in JP Application No. 2012-550069.
Office Action dated Apr. 24, 2013 in CN Application No. 201080040968.7.
Office Action dated Apr. 5, 2010 in U.S. Appl. No. 12/244,666.
Office Action dated Apr. 5, 2010 in U.S. Appl. No. 12/244,688.
Office Action dated Apr. 7, 2020 in Chinese Application No. 201880036318.1.
Office Action dated Aug. 10, 2017 in U.S. Appl. No. 14/372,384, by Cabiri.
Office Action dated Aug. 13, 2015 in U.S. Appl. No. 14/553,399 by Cabiri.

(56) References Cited

OTHER PUBLICATIONS

Office Action dated Aug. 13, 2018 in IN Application No. 857/KOLNP/2012.
Office Action dated Aug. 14, 2017 in CN Application No. 201410178318.9.
Office Action dated Aug. 15, 2013 in CN Application No. 200880117084.X.
Office Action dated Aug. 15, 2013 in U.S. Appl. No. 13/429,942 by Cabiri.
Office Action dated Aug. 26, 2014 in CN Application No. 201180006567.4.
Office Action dated Aug. 29, 2014 in JP Application No. 2012-550068.
Office Action dated Aug. 29, 2014 in JP Application No. 2012-550069.
Office Action dated Aug. 6, 2014 in EP Application No. 11 707 942.6.
Office Action dated Dec. 1, 2015 in CN Application No. 201410289204.1.
Office Action dated Dec. 10, 2013 in CN Application No. 201180006567.4.
Office Action dated Dec. 12, 2013 in JP Application No. 2012-529808.
Office Action dated Dec. 15, 2017 in U.S. Appl. No. 15/269,248, by Cabiri.
Office Action dated Dec. 15, 2020 in Japanese Application No. 2019-566222.
Office Action dated Dec. 29, 2016 in CN Application No. 201510695320.8.
Office Action dated Dec. 3, 2015 in CN Application No. 201280068544.0.
Office Action dated Dec. 4, 2017 in CN Application No. 201410178374.2.
Office Action dated Dec. 9, 2016 in U.S. Appl. No. 14/593,051, by Gross.
Office Action dated Feb. 15, 2017 in CN Application No. 201380027455.6.
Office Action dated Feb. 16, 2017 in CN Application No. 2014101783189.
Office Action dated Feb. 19, 2018 in EP Application No. 14789668.2.
Office Action dated Feb. 20, 2015 in U.S. Appl. No. 13/521,181 by Cabiri.
Office Action dated Feb. 21, 2012 in U.S. Appl. No. 12/689,249.
Office Action dated Feb. 24, 2015 in U.S. Appl. No. 14/258,661 by Cabiri.
Office Action dated Feb. 24, 2016 in U.S. Appl. No. 13/429,942 by Cabiri.
Office Action dated Feb. 24, 2017 in U.S. Appl. No. 13/964,651, by Gross.
Office Action dated Feb. 28, 2014 in CN Application No. 201180006571.0.
Office Action dated Feb. 4, 2014 in EP Application No. 11 707 942.6.
Office Action dated Jan. 10, 2017 in U.S. Appl. No. 14/193,692, by Gross.
Office Action dated Jan. 12, 2018 in EP Application No. 14789667.4.
Office Action dated Jan. 15, 2016 in U.S. Appl. No. 13/472,112 by Cabiri.
Office Action dated Jan. 16, 2014 in U.S. Appl. No. 13/429,942 by Cabiri.
Office Action dated Jan. 17, 2017 in EP Application No. 13716886.0.
Office Action dated Jan. 28, 2015 in U.S. Appl. No. 13/429,942 by Cabiri.
Office Action dated Jan. 30, 2013 in CN Application No. 200880117084.X.
Office Action dated Jan. 31, 2018 in U.S. Appl. No. 15/235,931, by Cabiri.
Office Action dated Jan. 4, 2016 in U.S. Appl. No. 13/892,905 by Cabiri.
Office Action dated Jan. 4, 2016 in U.S. Appl. No. 14/096,977 by Cabiri.
Office Action dated Jan. 5, 2016 in U.S. Appl. No. 14/696,644 by Cabiri.
Office Action dated Jan. 8, 2014 in U.S. Appl. No. 13/521,167 by Cabiri.
Office Action dated Jul. 13, 2011 in U.S. Appl. No. 12/559,563.
Office Action dated Jul. 2, 2012 in U.S. Appl. No. 13/272,555.
Office Action dated Jul. 22, 2020 in Japanese Application No. 2018-538074.
Office Action dated Jul. 23, 2018 in CN Application No. 201480054177.8.
Office Action dated Jul. 29, 2013 in JP Application No. 2012-529808.
Office Action dated Jul. 29, 2016 in U.S. Appl. No. 14/696,644, by Cabiri.
Office Action dated Jul. 3, 2017 in CN Application No. 201410178374.2.
Office Action dated Jul. 31, 2015 in U.S. Appl. No. 13/521,181 by Cabiri.
Office Action dated Jul. 7, 2014 in U.S. Appl. No. 12/244,666 by Gross.
Office Action dated Jul. 7, 2016 in U.S. Appl. No. 13/892,905 by Cabiri.
Office Action dated Jun. 1, 2016 in CN Application No. 201380027455.6.
Office Action dated Jun. 10, 2016 in U.S. Appl. No. 13/964,651 by Gross.
Office Action dated Jun. 14, 2018 in U.S. Appl. No. 13/874,121, by Degtiar.
Office Action dated Jun. 17, 2016 in CN Application No. 201280068544.0.
Office Action dated Jun. 2, 2016 in CN Application No. 2014101783189.
Office Action dated Jun. 3, 2014 in JP Application No. 2010-527595.
Office Action dated Jun. 3, 2021 in CN Application No. 201880034803.5.
Office Action dated Jun. 4, 2015 in U.S. Appl. No. 13/667,739 by Cabiri.
Office Action dated Jun. 9, 2017 in EP Application No. 14166591.9.
Office Action dated Jun. 9, 2017 in EP Application No. 14166596.8.
Office Action dated Mar. 1, 2018 in EP Application No. 14166592.7.
Office Action dated Mar. 10, 2015 in CN Application No. 201180006567.4.
Office Action dated Mar. 10, 2015 in U.S. Appl. No. 12/244,666 by Gross.
Office Action dated Mar. 10, 2015 in U.S. Appl. No. 13/643,470 by Alon.
Office Action dated Mar. 13, 2017 in U.S. Appl. No. 14/372,384, by Cabiri.
Office Action dated Mar. 15, 2018 in U.S. Appl. No. 29/628,592 by Cabiri.
Office Action dated Mar. 22, 2017 in CN Application No. 201480054191.8.
Office Action dated Mar. 23, 2015 in JP Application No. 2012-550068.
Office Action dated Mar. 30, 2018 in U.S. Appl. No. 14/850,450 by Gross.
Office Action dated Mar. 5, 2014 in CN Application No. 200880117084.X.
Office Action dated Mar. 7, 2017 in U.S. Appl. No. 14/696,644, by Cabiri.
Office Action dated May 1, 2015 in U.S. Appl. No. 14/638,525 by Filman.
Office Action dated May 13, 2015 in CN Application No. 201380025566.3.
Office Action dated May 14, 2018 in EP Application No. 08808111.2.
Office Action dated May 16, 2012 in U.S. Appl. No. 12/615,828.
Office Action dated May 17, 2016 in U.S. Appl. No. 13/886,867 by Cabiri.

(56) References Cited

OTHER PUBLICATIONS

Office Action dated May 18, 2015 in U.S. Appl. No. 13/429,942 by Cabiri.
Office Action dated May 18, 2016 in U.S. Appl. No. 13/667,739 by Cabiri.
Office Action dated May 18, 2018 in EP 14166591.9.
Office Action dated May 21, 2021 in JP Application No. 2018-538073.
Office Action dated May 23, 2013 in U.S. Appl. No. 13/063,236.
Office Action dated May 23, 2014 in U.S. Appl. No. 13/472,112 by Cabiri.
Office Action dated May 24, 2017 in CN Application No. 201380057196.1.
Office Action dated May 24, 2017 in U.S. Appl. No. 13/874,121, by Degtiar.
Office Action dated May 25, 2016 in U.S. Appl. No. 13/874,017 by Cabiri.
Office Action dated May 29, 2017 in EP Application No. 14789667.4.
Office Action dated May 3, 2012 in CN Application No. 200880117084.X.
Office Action dated May 31, 2016 in U.S. Appl. No. 14/593,051 by Gross.
Office Action dated May 4, 2017 in CN Application No. 201410183666.5.
Office Action dated May 5, 2015 in CN Application No. 201180006571.0.
Office Action dated Nov. 10, 2016 in U.S. Appl. No. 13/874,121, by Degtiar.
Office Action dated Nov. 13, 2017 in U.S. Appl. No. 14/193,692, by Gross.
Office Action dated Nov. 14, 2017 in U.S. Appl. No. 14/593,041, by Cabiri.
Int'l Preliminary Report on Patentability dated May 26, 2015 in Int'l Application No. PCT/US2012/066036.
Int'l Preliminary Report on Patentability dated Nov. 3, 2015 in Int'l Application No. PCT/US14/35662.
Int'l Search Report (Partial), dated Dec. 20, 2016 in Int'l Application No. PCT/US2016/056247.
Int'l Search Report and Written Opinion dated Apr. 21, 2017 in Int'l Application No. PCT/US2016/068367.
Int'l Search Report and Written Opinion dated Apr. 3, 2014 in Int'l Application No. PCT/US2013/078040.
Int'l Search Report and Written Opinion dated Apr. 5, 2013 in Int'l Application No. PCT/US2012/050696.
Int'l Search Report and Written Opinion dated Aug. 12, 16 in Int'l Application No. PCT/US2016/035720.
Int'l Search Report and Written Opinion dated Aug. 14, 2018 in Int'l Application No. PCT/US2018/034882.
Int'l Search Report and Written Opinion dated Aug. 28, 2014 in Int'l Application No. PCT/US2014/035662.
Int'l Search Report and Written Opinion dated Aug. 5, 2013 in Int'l Application No. PCT/US2013/033118.
Int'l Search Report and Written Opinion dated Aug. 6, 2018 in Int'l Application No. PCT/US2018/035000.
Int'l Search Report and Written Opinion dated Dec. 12, 2014 in Int'l Application No. PCT/US2014/058433.
Int'l Search Report and Written Opinion dated Dec. 15, 2016 in Int'l Application No. PCT/US2016/056258.
Int'l Search Report and Written Opinion dated Dec. 2, 2016 in Int'l Application No. PCT/US2016/056210.
Int'l Search Report and Written Opinion dated Dec. 5, 2016 in Int'l Application No. PCT/US2016/056233.
Int'l Search Report and Written Opinion dated Dec. 8, 2016 in Int'l Application No. PCT/US2016/056227.
Int'l Search Report and Written Opinion dated Jan. 12, 2011 in Int'l Application No. PCT/US2010/048556; Written Opinion.
Int'l Search Report and Written Opinion dated Jan. 26, 2017 in Int'l Application No. PCT/US2016/056213.
Int'l Search Report and Written Opinion dated Jan. 7, 2014 in Int'l Application No. PCT/US2013/065211.
Int'l Search Report and Written Opinion dated Jul. 12, 2017 in Int'l Application No. PCT/US2016/056238.
Int'l Search Report and Written Opinion dated Jul. 31, 2014 in Int'l Application No. PCT/US2014/033598.
Int'l Search Report and Written Opinion dated Jul. 6, 2017 in Int'l Application No. PCT/US2017/022966.
Int'l Search Report and Written Opinion dated Jun. 30, 2014 in Int'l Application No. PCT/US2013/031598.
Int'l Search Report and Written Opinion dated Mar. 2, 2015 in Int'l Application No. PCT/US2014/058446.
Int'l Search Report and Written Opinion dated Mar. 27, 2017 in Int'l Application No. PCT/US2016/056247.
Int'l Search Report and Written Opinion dated May 13, 2009 in Int'l Application No. PCT/IL2008/001312.
Int'l Search Report and Written Opinion dated May 15, 2017 in Int'l Application No. PCT/US2016/068371.
Int'l Search Report and Written Opinion dated Nov. 28, 2016 in Int'l Application No. PCT/US2016/056218.
Int'l Search Report and Written Opinion dated Nov. 30, 2016 in Int'l Application No. PCT/US2016/056223.
Int'l Search Report and Written Opinion dated Nov. 5, 2012 in Int'l Application No. PCT/US2012/039465.
Int'l Search Report and Written Opinion dated Sep. 18, 2018 in Int'l Application No. PCT/US2018/035107.
Int'l Search Report and Written Opinion dated Apr. 26, 2017 in Int'l Application No. PCT/US2016/068049.
Int'l Search Report and Written Opinion dated Jul. 26, 2013 in Int'l Application No. PCT/US2013/039465.
Int'l Search Report and Written Opinion dated May 27, 2015 in Int'l Application No. PCT/US2014/058456.
Int'l Search Report dated Apr. 20, 2017 in Int'l Application No. PCT/US2016/068058.
Int'l Search Report dated Apr. 26, 2010 in Int'l Application No. PCT/US2009/069552.
Int'l Search Report dated Aug. 11, 2010 in Int'l Application No. PCT/US2009/056778.
Int'l Search Report dated Jun. 17, 2011 in Int'l Application No. PCT/US2011/021604.
Int'l Search Report dated Oct. 12, 2011 in Int'l Application No. PCT/US2011/021605.
Int'l Search Report dated Sep. 22, 2011 in Int'l Application No. PCT/IL11/00368; Written Opinion.
Int'l Written Opinion dated Jul. 19, 2012 in Int'l Application No. PCT/US2011/021605.
International Preliminary Report on Patentability and Written Opinion dated Jul. 5, 2011 in International Application No. PCT/US2009/069552.
International Search Report dated Jul. 30, 2013 in International Application No. PCT/US2012/066036.
Liao, et al., "Research progress of needle stick protective equipment," General Nursing, 2011, No. 28, 2 pages.
Notice of Allowance dated Aug. 24, 2015 in U.S. Appl. No. 29/479,307 by Norton.
Notice of Allowance datead Apr. 25, 2016 in U.S. Appl. No. 14/553,399 by Cabiri.
Notice of Allowance dated May 11, 2016 in U.S. Appl. No. 14/931,439 by Cabiri.
Office Action dated Apr. 19, 2016 in U.S. Appl. No. 14/372,384, by Cabiri.
Office Action dated Apr. 20, 2017 in U.S. Appl. No. 13/886,867, by Cabiri.
Office Action dated Apr. 22, 2016 in CN Application No. 2014102892041.
Adler et al, "Pulse Width Modulation", Electronics in Meccano, No. 6, Published Jan. 2000, retrieved from http://www.eleinmec.com/article.asp?28 on Jul. 3, 2023.
Chan et al.; "Manufacturing Consideration in Developing a Prefilled Syringe Investigating the Effect of Headspace Pressure"; American Pharmaceutical Review, downloaded from webpage <https://www.americanpharmaceuticalreview.com/Featured-Articles/112325-

(56) References Cited

OTHER PUBLICATIONS

Manufacturing-Consideration-in-Developing-a-Prefilled-Syringe-Investigating-the-Effect-of-Headspace-Pressure/>, May 8, 2012, 7 pages.
Communication Pursuant to Rules 161 and 162 dated Apr. 6, 2018 in EP Application No. 16784688.0. 3 pages.
Copaxone®, Innovative Drugs, Teva Pharmaceuticals, downloaded from webpage: http://tevapharm.com/copaxone/, Download date: Jan. 2009, original posting date: unknown, 3 pages.
Daikyo Crystal Zenith® polymer, Manufactured by Daikyo Seiko, Ltd. (Jun. 25, 2008). 2 pages.
Definition of Monolithic. In Merriam-Webster's online dictionary. Retrieved from https://www.merriam-webster.com/dictionary/monolithic (Year 2021).
Edwards et al., "Appendix 3 Measurement of Leakage of Tuberculin Syringes"; World Health Organization Monograph Series No. 12; BCG Vaccination, Tuberculosis Research Office World Health Organization Copenhagen; World Health Organization; Palais Des Nations, Geneva, 1953. 15 pages.
European Search Report (Partial) dated Mar. 8, 2017 in EP Application 16193157.1. 7 pages.
Examination Report dated May 8, 2017 in EP Application No. 12750951.1. 4 pages.
Extended European Search Report dated Aug. 7, 2014 in EP Application No. 1417477.4. 7 pages.
Extended European Search Report dated Feb. 12, 2018 in EP Application No. 17191756.0. 8 pages.
Extended European Search Report dated Feb. 13, 2017 in EP Application No. 16171626.1. 9 pages.
Extended European Search Report dated Feb. 23, 2015 in EP Application No. 14166596.8. 6 pages.
Extended European Search Report dated Feb. 23, 2015 in EP Application No. 14166591.9. 6 pages.
Extended European Search Report dated Jan. 20, 2017 in EP Application No. 16164319.2. 5 pages.
Extended European Search Report dated Jul. 28, 2020 in European Application No. 20172466.3. 8 pages.
Extended European Search Report dated Jul. 3, 2017 in EP Application No. 16190054.3. 7 pages.
Extended European Search Report dated Mar. 27, 2014 in EP Application No. 14154717.4. 6 pages.
Extended European Search Report dated Mar. 8, 2016 in EP Application No. 14166592.7. 11 pages.
Extended European Search Report dated Nov. 10, 2016 in EP Application No. 08808111.2. 9 pages.
Extended Search Report dated Jul. 3, 2017 in EP Application No. 16200040.0. 4 pages.
Extended Search Report dated Jul. 7, 2017 in EP Application No. 16193157.1. 14 pages.
Extended Search Report dated Jun. 13, 2016 in EP Application No. 16157430.6. 7 pages.
Int'l Preliminary Examination Report dated Apr. 5, 2016 in Int'l Application No. PCT/US2014/058433.
Int'l Preliminary Examination Report dated Apr. 5, 2016 in Int'l Application No. PCT/US2014/058446.
Int'l Preliminary Examination Report dated Apr. 5, 2016 in Int'l Application No. PCT/US2014/058456.
Int'l Preliminary Report of Patentability dated Aug. 16, 2019 in Int'l Application No. PCT/US2018/034882.
Int'l Preliminary Report on Patentability date Jan. 8, 2018 in Int'l Application No. PCT/US2016/056218.
Int'l Preliminary Report on Patentability dated Apr. 7, 2010 in Int'l Application No. PCT/IL2008/001312.
Int'l Preliminary Report on Patentability dated Aug. 14, 2014 in Int'l Application No. PCT/US2012/050696.
Int'l Preliminary Report on Patentability dated Aug. 2, 2012 in Int'l Application No. PCT/US2011/021604.
Int'l Preliminary Report on Patentability dated Dec. 5, 2017 in In'tl Application No. PCT/US2016/035720.
Int'l Preliminary Report on Patentability dated Feb. 5, 2019 in Int'l Application No. PCT/US2016/068058.
Int'l Preliminary Report on Patentability dated Feb. 7, 2013 in Int'l Application No. PCT/US2011/021604.
Int'l Preliminary Report on Patentability dated Feb. 7, 2013 in Int'l Application No. PCT/US2011/021605.
Int'l Preliminary Report on Patentability dated Jan. 18, 2018 in Int'l Application No. PCT/US2016/056210.
Int'l Preliminary Report on Patentability dated Jan. 18, 2018 in Int'l Application No. PCT/US2016/056213.
Int'l Preliminary Report on Patentability dated Jan. 18, 2018 in Int'l Application No. PCT/US2016/056223.
Int'l Preliminary Report on Patentability dated Jan. 18, 2018 in Int'l Application No. PCT/US2016/056227.
Int'l Preliminary Report on Patentability dated Jan. 9, 2011 in Int'l Application No. PCT/US2010/048556.
Int'l Preliminary Report on Patentability dated Jul. 16, 2015 in Int'l Application No. PCT/US2013/078040.
Int'l Preliminary Report on Patentability dated Mar. 15, 2011 in Int'l Application No. PCT/US2009/056778.
Int'l Preliminary Report on Patentability dated May 14, 2015 in Int'l Application No. PCT/US2013/065211.
Int'l Preliminary Report on Patentability dated Nov. 22, 2017 in Int'l Application No. PCT/US2016/068371.
Int'l Preliminary Report on Patentability dated Nov. 27, 2014 in Int'l Application No. PCT/US2013/039465.
Int'l Preliminary Report on Patentability dated Nov. 30, 2017 in Int'l Application No. PCT/US2016/068367.
Int'l Preliminary Report on Patentability dated Nov. 9, 2018 in Int'l Application No. PCT/US2016/056238.
Int'l Preliminary Report on Patentability dated Oct. 1, 2014 in Int'l Application No. PCT/US13/31598.
Int'l Preliminary Report on Patentability dated Oct. 9, 2014 in Int'l Application No. PCT/US2013/033118.
Int'l Preliminary Report on Patentability dated Sep. 1, 2011 in Int'l Application No. PCT/US2010/048556.
Office Action dated Nov. 16, 2015 in U.S. Appl. No. 13/733,516 by Cabiri.
Office Action dated Nov. 16, 2017 in CN Application No. 201480054191.8.
Office Action dated Nov. 17, 2017 in U.S. Appl. No. 14/510,846, by Cabiri.
Office Action dated Nov. 2, 2014 in CN Application No. 201180006571.0.
Office Action dated Nov. 2, 2016 in CN Application No. 2013800571961.
Office Action dated Nov. 21, 2014 in U.S. Appl. No. 13/429,840 by Cabiri.
Office Action dated Nov. 21, 2014 in U.S. Appl. No. 13/472,112 by Cabiri.
Office Action dated Nov. 25, 2015 in U.S. Appl. No. 14/372,384 by Cabiri.
Office Action dated Nov. 25, 2016 in U.S. Appl. No. 13/874,017, by Cabiri.
Office Action dated Nov. 29, 2019 in CN Application No. 201680032632.3.
Office Action dated Nov. 4, 2013 in EP Application No. 11 709 234.6.
Office Action dated Nov. 5, 2013 in JP Application No. 2010-527595.
Office Action dated Nov. 5, 2014 in U.S. Appl. No. 13/643,470 by Alon.
Office Action dated Nov. 6, 2015 in U.S. Appl. No. 14/715,791 by Cabiri.
Office Action dated Nov. 8, 2017 in U.S. Appl. No. 13/874,121, by Degtiar.
Office Action dated Nov. 9, 2016 in U.S. Appl. No. 14/683,253, by Cabiri.
Office Action dated Oct. 11, 2017 in U.S. Appl. No. 29/605,061, by Cabiri.
Office Action dated Oct. 17, 2012 in U.S. Appl. No. 13/063,236.
Office Action dated Oct. 28, 2011 in U.S. Appl. No. 12/615,828.

(56) References Cited

OTHER PUBLICATIONS

Office Action dated Oct. 28, 2015 in U.S. Appl. No. 13/429,942 by Cabiri.
Office Action dated Oct. 28, 2016 in CN Application No. 201410178374.2.
Office Action dated Oct. 5, 2017 in U.S. Appl. No. 29/605,068, by Cabiri.
Office Action dated Oct. 6, 2017 in U.S. Appl. No. 14/861,478, by Cabiri.
Office Action dated Oct. 6, 2017 in U.S. Appl. No. 29/604,616, by Cabiri.
Office Action dated Oct. 6, 2017 in U.S. Appl. No. 29/605,051, by Cabiri.
Office Action dated Oct. 7, 2015 in U.S. Appl. No. 14/186,403 for Cabiri.
Office Action dated Oct. 9, 2013 in IL Application No. 208634.
Office Action dated Oct. 9, 2014 in U.S. Appl. No. 13/873,335.
Office Action dated Oct. 9, 2020 in JP Application No. 2018-538073.
Office Action dated Sep. 13, 2017 in EP Application No. 13783458.6.
Office Action dated Sep. 18, 2015 in U.S. Appl. No. 13/874,085 by Cabiri.
Office Action dated Sep. 2, 2010 in U.S. Appl. No. 12/244,688.
Office Action dated Sep. 21, 2010 in U.S. Appl. No. 12/244,666.
Office Action dated Sep. 26, 2018 in JP Application No. 2018-535062.
Office Action dated Sep. 28, 2017 in IN Application No. 2528/DELNP/2010.
Office Action dated Sep. 29, 2013 in CN Application No. 201080040968.7.
Office Action dated Sep. 29, 2020 in JP Application No. 2018-538527.
Office Action dated Sep. 30, 2010 in U.S. Appl. No. 12/689,250.
Office Action dated Sep. 30, 2015 in U.S. Appl. No. 13/667,739 by Cabiri.
Office Action dated Sep. 30, 2016 in U.S. Appl. No. 13/886,867, by Cabiri.
Office Action dated Sep. 30, 2020 in CN Application No. 201780033863.0.
Office Action dated Sep. 6, 2011 in U.S. Appl. No. 12/345,818.
Office Action dated Sep. 8, 2017 is U.S. Appl. No. 15/510,846, by Aida.
Office Action dated Sep. 9, 2015 in U.S. Appl. No. 13/643,470 by Alon.
Office Action dated Aug. 17, 2021 in IN Application No. 201827027625.
Office Action dated Dec. 17, 2015 in CN Application No. 201380017192.0.
Office Action dated Feb. 19, 2016 in U.S. Appl. No. 14/553,399 by Cabiri.
Office Action dated Feb. 3, 2016 in U.S. Appl. No. 14/931,439 by Cabiri.
Office Action dated Jan. 8, 2013 in JP Application No. 2010-527595.

\* cited by examiner

MODULAR DRIVE TRAIN FOR WEARABLE INJECTOR

CROSS-REFERENCE TO RELATED APPLICATIONS

This application is a section 371 of International Application No. PCT/US2018/034597, filed May 25, 2018, which was published on Dec. 6, 2018 under International Publication No. WO 2018/222521A1, and which claims priority to U.S. Provisional Patent Application No. 62/512,505, titled "Modular Drive Train Installation—Bearing Snap to Allow TSA Reversal", filed on May 30, 2017, the entire contents of each of which are incorporated by reference herein.

BACKGROUND OF THE DISCLOSURE

The present disclosure is generally directed to a modular drive train, and, more particularly, to a modular drive train securable in a wearable injector.

Wearable injectors are complex medical devices comprising numerous interconnected operational components assembled therein. Typically, for example, injector drive trains, utilized to drive and dispense substance from a reservoir within the injector, through an injection needle or cannula, to a user, comprise multiple operationally interconnected complex parts. As is well known, the cost of the operational components and assembly thereof, as well as the cost of quality control procedures employed to minimize manufacture and delivery of substandard devices contributes to the cost of medical devices to consumers.

Accordingly, it is desirable to minimize cost of components and maximize ease of device assembly. Constructing the device from a plurality of removable modules may assist in both simplicity of assembly (by assembling individual modules prior to assembly into the device), as well as simplicity of replacing faulty components/modules as part of quality control. Moreover, constructing the module from polymeric components may further reduce cost.

Therefore, it would be advantageous to manufacture a modular drive train assembly securable to an injector, which may be comprised at least partially of polymeric components.

BRIEF SUMMARY OF THE DISCLOSURE

Briefly stated, one aspect of the present disclosure is directed to a modular drive train for a wearable injector housing a cartridge therein, wherein the cartridge is sealed at one end by a piston. The drive train comprises a chassis selectively securable within the injector, and a telescoping driving assembly mounted within the chassis. The telescoping driving assembly comprises a first shaft rotatable relative to the chassis, and a second shaft telescopically connected with the first shaft and axially movable relative to the first shaft. Rotation of the first shaft axially drives the second shaft from a retracted configuration to an extended configuration to engage and advances the piston within the cartridge. The second shaft is rotatably fixed relative to the chassis. The chassis includes one of a bearing and an elastically expandable collar projecting axially forward into the chassis from a rear end of the chassis, and the first shaft includes another of the bearing and the elastically expandable collar projecting axially rearwardly from a rear end of the first shaft. The collar is configured to elastically snap over an interference element of the bearing, whereby engagement of the collar with the bearing axially secures the first shaft to the chassis and permits rotation of the first shaft about the bearing.

Another aspect of the present disclosure is directed to a modular drive train for a wearable injector housing a cartridge therein wherein the cartridge is sealed at one end by a piston. The drive train comprises a telescoping driving assembly and an actuator. The telescoping driving assembly comprises a rotatable first shaft, and a second shaft telescopically connected with the first shaft and axially movable relative to the first shaft. Rotation of the first shaft axially drives the second shaft from a retracted configuration to an extended configuration to engage and advance the piston within the cartridge. The second shaft is rotatably fixed. The actuator rotates the first shaft of the telescoping driving assembly. A chassis is selectively securable within the injector. The chassis comprises a first sleeve and a second sleeve generally parallel to the first sleeve. The telescoping driving is slidably received within the first sleeve, and the first shaft is axially secured to the first sleeve. The actuator is slidably received within the second sleeve.

BRIEF DESCRIPTION OF THE DRAWINGS

The following detailed description of aspects of the disclosure will be better understood when read in conjunction with the appended drawings. It should be understood, however, that the invention is not limited to the precise arrangements and instrumentalities shown. In the drawings.

DETAILED DESCRIPTION OF THE DISCLOSURE

Figure 1:
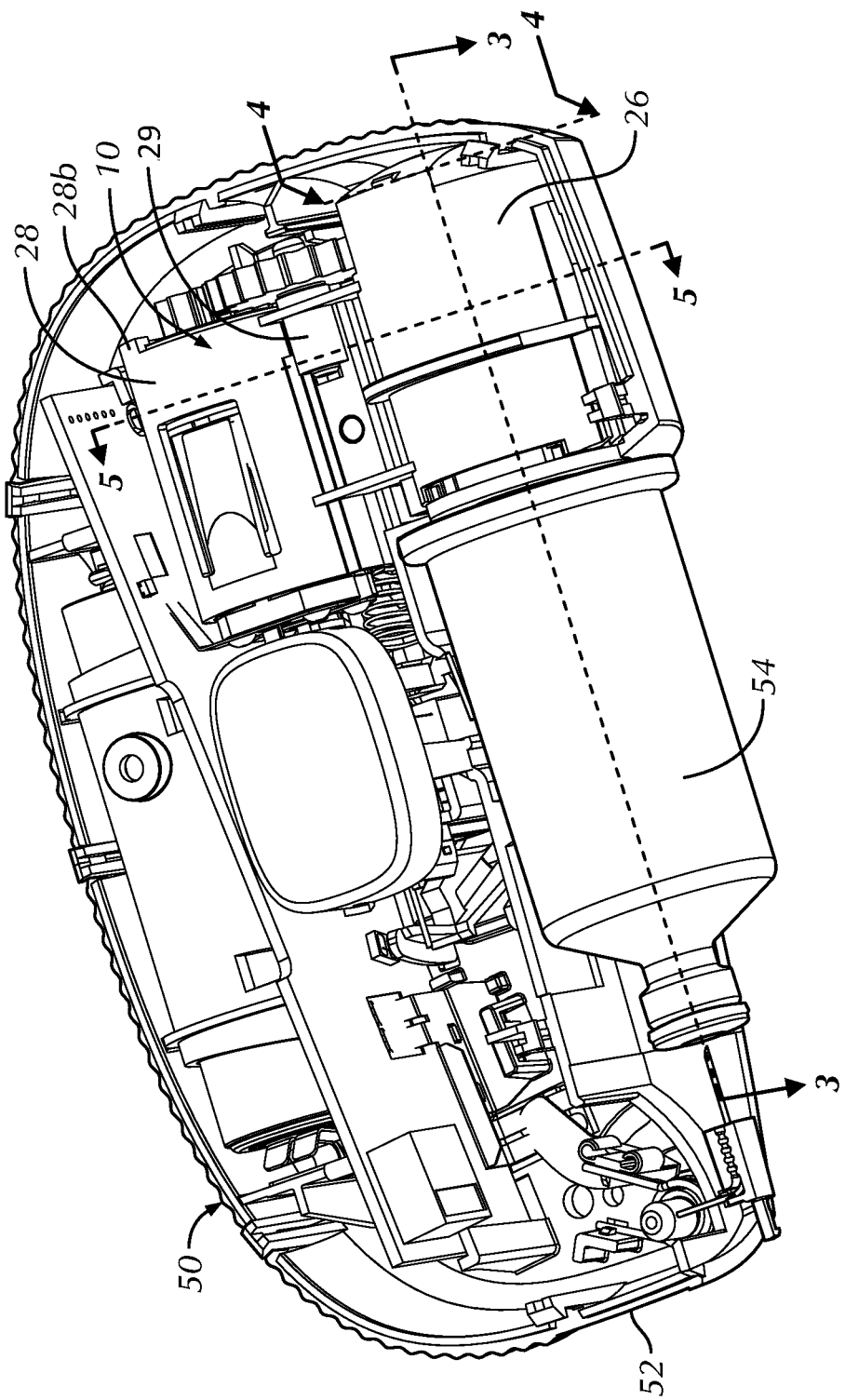
FIG. 1 is a partial perspective view of a wearable injector, having a modular drive train in accordance with an embodiment of the present disclosure secured therein.

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the modular drive train, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Figure 2:
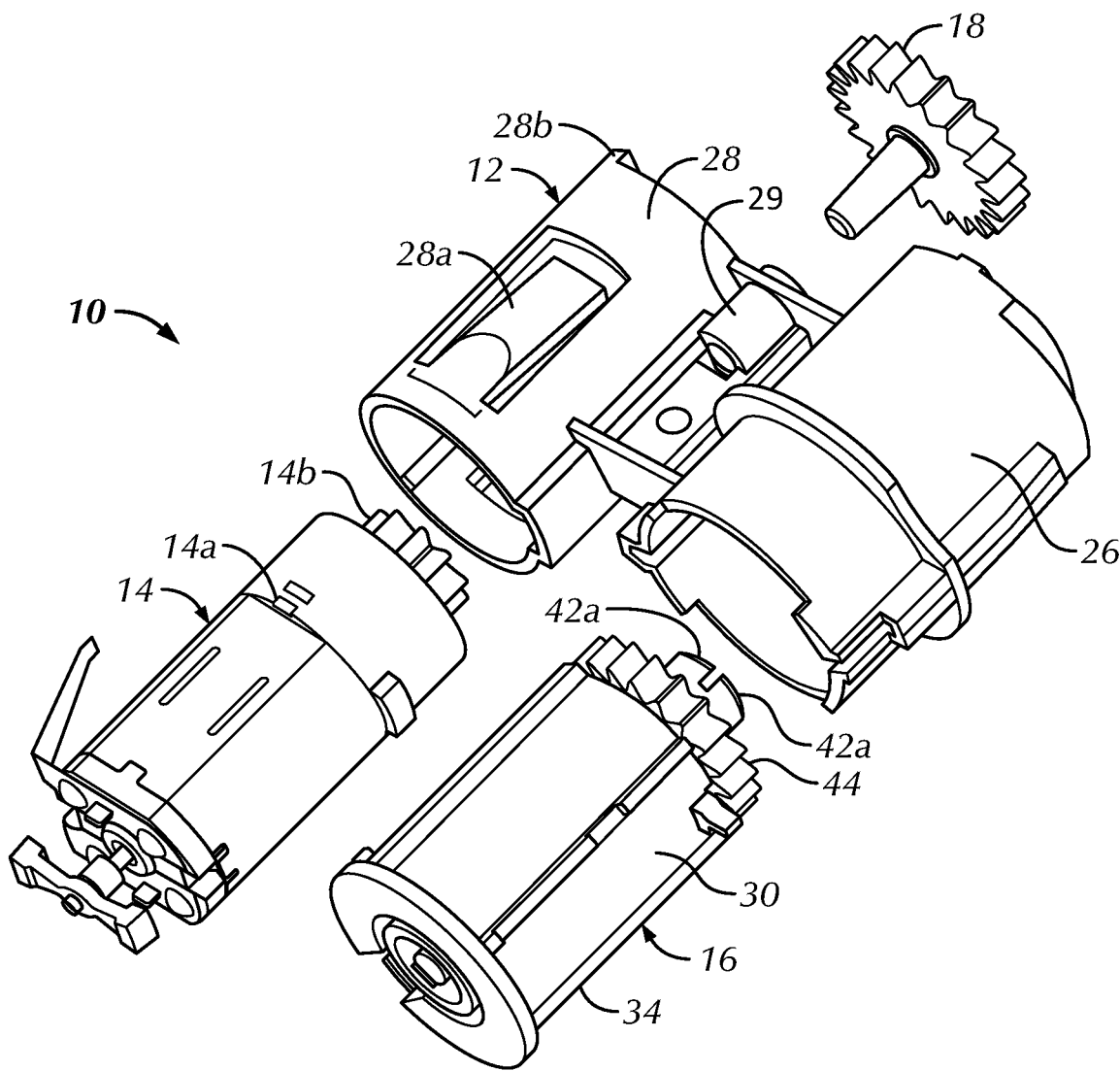
FIG. 2 is a partially exploded perspective view of the modular drive train of FIG. 1.
Figure 3:
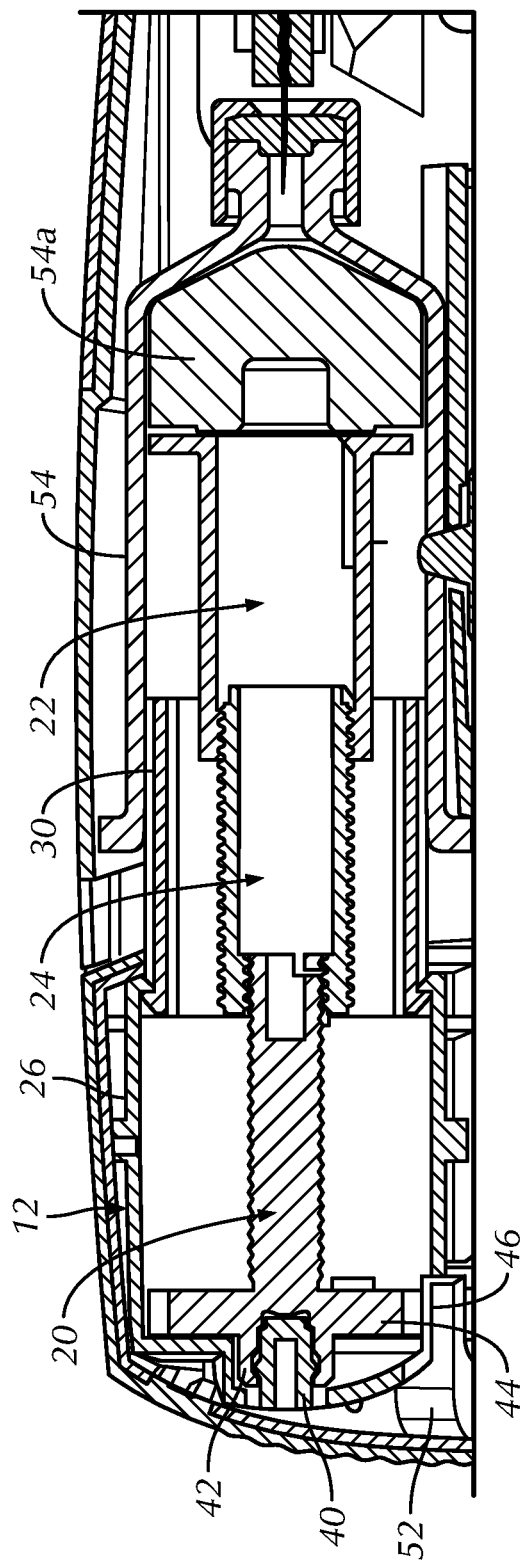
FIG. 3 is a partial cross-sectional view of the modular drive train of FIG. 1, taken along the sectional line 3-3 of FIG. 1, with a telescoping driving assembly thereof in an extended configuration.

Referring to the drawings in detail, wherein like numerals indicate like elements throughout, there is shown in FIGS. 1-5 a modular drive train, generally designated 10, in accordance with an embodiment of the present disclosure. Generally, the modular drive train 10 is utilized in a wearable injector (patch injector) 50, such as, for example, without limitation, a wearable drug injector. As should be understood by those of ordinary skill in the art, and as best shown in FIG. 1, a wearable injector generally comprises a housing 52 that houses a cartridge or reservoir 54 containing a substance therein, wherein the cartridge 54 is sealed at one end by a piston 54a (FIG. 3). The cartridge 54 is fluidly connectable to an injection needle (not shown), to dispense the substance within the cartridge 54 through the needle to a user.

As shown in FIG. 2, the modular drive train 10 comprises a chassis 12, selectively securable within the housing 52 of the injector 50, an actuator 14, a telescoping driving assembly 16, and a transmission gear 18. In one embodiment, the chassis 12 may be removably secured within the housing 52. Alternatively, the chassis 12 may be permanently, i.e., non-removably, secured within the housing 52, such as, for example, without limitation, via bonding or welding. The actuator 14 and the telescoping driving assembly 16 are mounted within the chassis 12 (as will be explained in further detail below). In the illustrated embodiment, the actuator 14 takes the form of a motor, but the present disclosure is not so limited. For example, the actuator 14 may take the form of a spring actuator, a gaseous actuator, a chemical actuator, an electrical actuator, an electromechanical actuator, combinations thereof, or the like. The actuator 14 drives expansion of the telescoping driving assembly 16 and is connected to the telescoping driving assembly 16 via the transmission gear 18 (as will be explained in further detail below).

The chassis 12 includes a first sleeve 26 and a second sleeve 28 generally parallel to the first sleeve 26, with a third sleeve 29 therebetween. The telescoping driving assembly 16 is slidably received within the first sleeve 26, the actuator 14 is slidably received within the second sleeve 28 and the transmission gear 18 is mounted to the third sleeve 29. The second sleeve 28 generally corresponds in size and shape to the actuator 14. In the illustrated embodiment, the actuator 14 and the second sleeve 28 include complementary, i.e., reciprocal, snap connection components 14a, 28a, respectively, to slidably secure and lock the actuator 14 into the second sleeve 28. As shown best in FIG. 2, the snap component 28a of the second sleeve 28 takes the form of a flexible member projecting progressively inwardly from the sidewall of the second sleeve 28 toward the radial center of the second sleeve 28. The flexible member 28a extends progressively further inwardly along an insertion direction of the actuator 14. The snap component 14a of the actuator 14 takes the form of a radial lip or shoulder. Accordingly, as the actuator 14 is inserted into the second sleeve 28, the radial lip 14a elastically biases the flexible member 28a outward, and upon sliding past the flexible member 28a, the flexible member 28a snaps back into the original orientation thereof, abutting the radial lip 14a and securing the actuator 14 within the second sleeve 28, i.e., preventing retraction of the actuator 14 in a direction opposite from the insertion direction thereof. As should be understood by those of ordinary skill in the art, however, the actuator 14 may be secured to the second sleeve 28 via other coupling methods, currently known or that later become known. The second sleeve 28 also includes a stop member 28b at a rear end thereof to abut the actuator 14 when inserted. In the illustrated embodiment, the stop member 28b takes the form of a radially inwardly extending lip, but the disclosure is not so limited. Advantageously, no additional tools are required for securing the actuator 14 within the second sleeve 28.

Turning to the telescoping driving assembly 16, the telescoping driving assembly 16 is configured to engage and advance the piston 54a through the cartridge 54 to expel the substance out of the cartridge 54. One non-limiting example of a telescoping driving assembly 16 is described in U.S. patent application Ser. No. 14/725,009, entitled, "Linear Rotation Stabilizer For A Telescoping Syringe Stopper Driverdriving Assembly," the entire contents of which are incorporated by reference herein.

In the illustrated embodiment, and as shown best in FIG. 3, the telescoping driving assembly 16 includes a first shaft 20 and a second shaft 22 telescopically connected with the first shaft 20 and axially movable relative to the first shaft 20. Rotation of the first shaft 20 axially drives the second shaft 22 from a retracted configuration (FIGS. 2, 4A, 4B) to an extended configuration (FIG. 3) to engage and advance the piston 54a through the cartridge 54. In the illustrated embodiment, as shown best in FIG. 3, an optional third shaft 24 is threadedly connected to the first shaft 20 and threadedly connected to the second shaft 22, connecting the first shaft 20 with the second shaft 22. Thus, rotation of the first shaft 20 rotates and axially drives the third shaft 24, which, in turn, axially drives the second shaft 22 (as will be explained further below).

As shown best in FIGS. 3-5, the first shaft 20 is received within, and axially secured to, the first sleeve 26 (as will be explained further below). The telescoping driving assembly 16 further includes an anti-rotation sleeve 30 rotationally fixed and axially slidable relative to both the first sleeve 26 and the second shaft 22. For example, as shown in FIG. 5, the first sleeve 26 of the chassis 12 is generally concentric with the anti-rotation sleeve 30, which is generally concentric with the second shaft 22 (at least in the retracted configuration of the driving assembly 16). In the illustrated embodiment, the anti-rotation sleeve 30 is keyed to the first sleeve 26, and the second shaft 22 is keyed to the anti-rotation sleeve 30. In particular, the first sleeve 26 defines at least one axially extending slot 32 along the interior sidewall thereof, and the anti-rotation sleeve 30 includes at least one corresponding rib 34 radially outwardly extending into the slot 32. The rib 34, being slidable along the slot 32, permits axial movement of the anti-rotation sleeve 30 relative to the first sleeve 26 of the chassis 12, while preventing relative rotation therebetween.

Similarly, the anti-rotation sleeve 30 defines at least one axially extending slot 36 along the interior sidewall thereof, and the second shaft 22 includes at least one corresponding rib 38 radially outwardly extending into the slot 36. The rib 38, being slidable along the slot 36, permits axial movement of the second shaft 22 relative to the anti-rotation sleeve 30, while preventing relative rotation therebetween. Accordingly, the second shaft 22 is rotatably fixed and axially slidable relative to the first sleeve 26 of the chassis 12, via the anti-rotation sleeve 30. As should be understood by those of ordinary skill in the art, however, the second shaft 22 may be rotatably fixed and axially slidable relative to the chassis 12 via other coupling methods, currently known or that later become known. The third shaft 24, being threadedly connected to each of the first shaft 20 and the second shaft 22 is, therefore, rotatable and axially movable relative to the first shaft 20. The second shaft 22 is axially movable relative to the first shaft 20 and the third shaft 24. Accordingly, the first, third and second shafts 20, 24, 22 form an axially telescoping assembly.

Figure 4A:
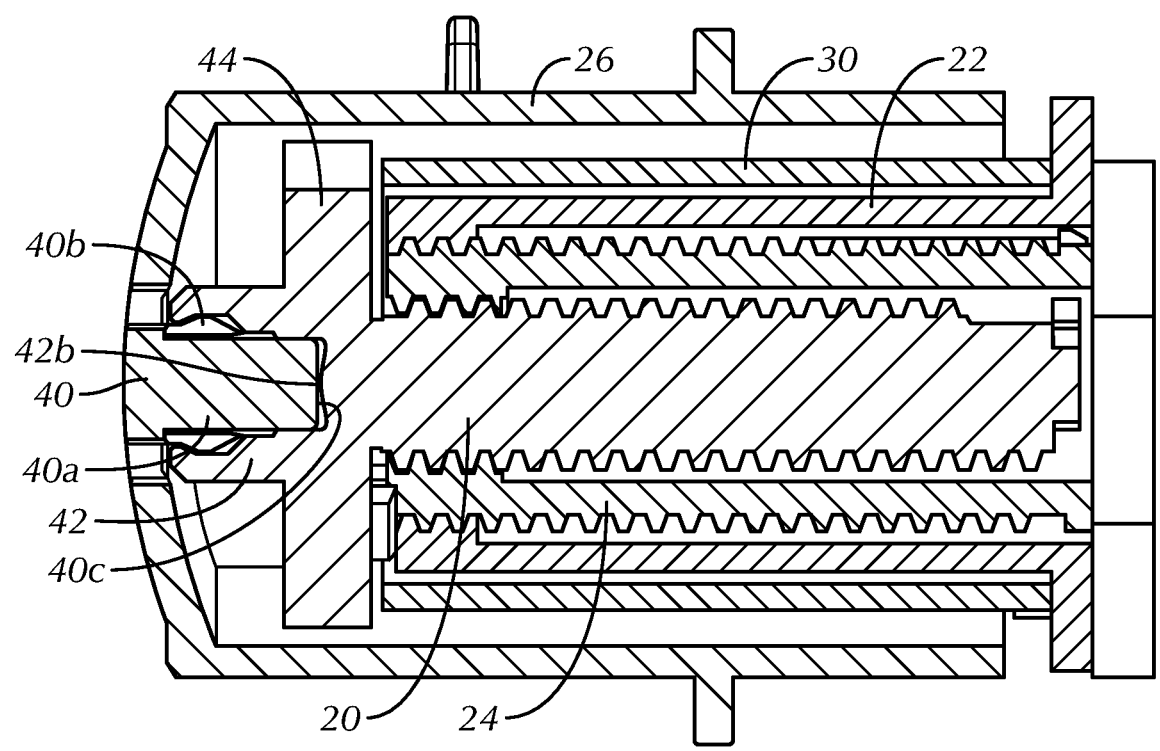
FIG. 4A is a cross-sectional view of a first sleeve of the modular drive train of FIG. 1, taken along the sectional line 4-4 of FIG. 1, with the telescoping driving assembly in a retracted configuration.
Figure 4B:
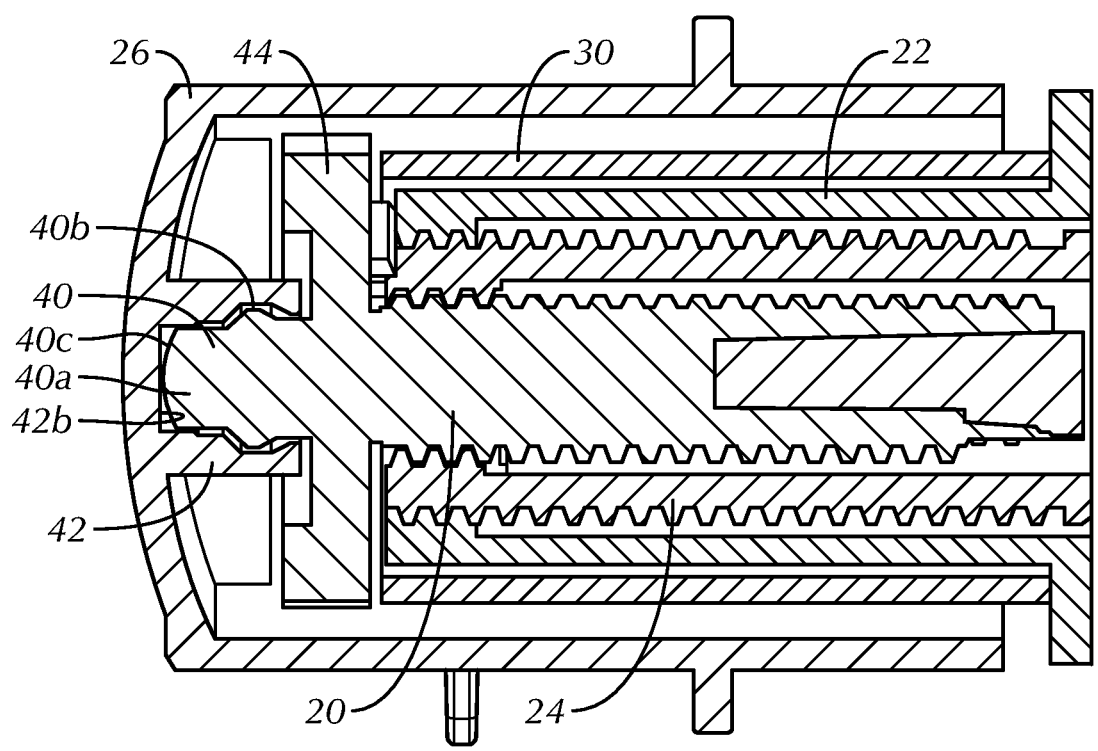
FIG. 4B is a cross-sectional view of an alternative configuration of the first sleeve of the modular drive train of FIG. 1, taken along the sectional line 4-4 of FIG. 1, with an alternative configuration of the telescoping driving assembly in a retracted configuration.
Figure 5:
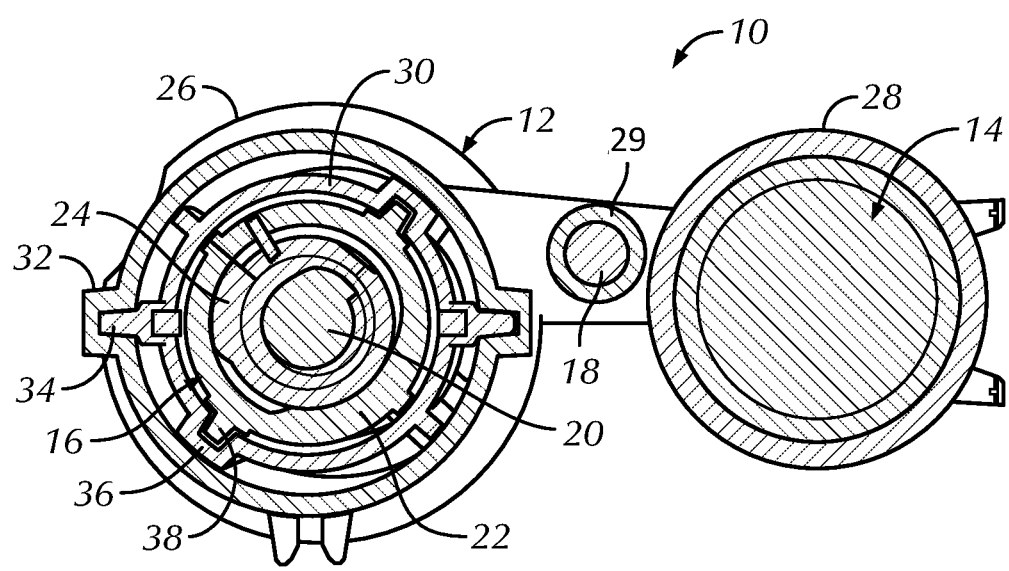
FIG. 5 is a cross-sectional view of the modular drive train of FIG. 1, taken along the sectional line 5-5 of FIG. 1.

Turning to FIGS. 3-4B, the first sleeve 26 generally corresponds in size and shape to the telescoping driving assembly 16, for slidably receiving the telescoping driving assembly 16 therein. As shown in FIG. 4A, the first sleeve 26 includes a bearing 40 projecting axially forward, i.e., inwardly into the first sleeve 26 from a rear end thereof. The first shaft 20 includes a corresponding elastically expandable collar 42 projecting axially rearwardly from a rear end of the first shaft 20. The collar 42 is configured to elastically snap over an interference element 40b of the bearing 40, i.e., expand over the interference element 40b and, thereafter, retract substantially back to the original configuration thereof. Advantageously, the position of the bearing 40 self-aligns the telescoping driving assembly 16 with the first sleeve 26 without added connectors or tools, when the collar 42 is engaged with the bearing 40.

As shown in FIG. 4A, the bearing 40 comprises a generally rod-shaped core 40a, and the interference element 40b takes the form of at least one radially outwardly projecting tab on the rod-shaped core 4a. In one embodiment, the tab(s) 40b may take the form of an annular lip about the rod-shaped core 40a. As shown best in FIG. 2, the corresponding collar 42 is substantially cylindrical and comprises a plurality of angularly spaced and radially outwardly flexible arcuate members 42a. In the illustrated embodiment the arcuate members 42a take the form of two diametrically opposed semi-circular members 42a, but the present disclosure is not so limited. The arcuate members 42a elastically flex radially outwardly upon engaging the tab(s) 40b and snap back over the tab(s) 40b to secure the first shaft 20 to the first sleeve 26. Alternatively, the collar 42 may take the form of a substantially contiguous cylinder, elastically expandable at least partly as a result of the material properties thereof. Engagement of the collar 42 with the bearing 40 permits rotation of the first shaft 20 about the bearing 40 to drive the telescoping driving assembly 16 while axially securing the first shaft 20 to the first sleeve 26 during axial expansion of the telescoping driving assembly 16 (to advance the piston 54a) or during axial retraction of the telescoping driving assembly 16. That is, rotation of the first shaft 20 relative to the third shaft 24 causes the third shaft 24 to advance axially forward, and rotation of the third shaft 24 relative to the second shaft 22 causes the second shaft 22 to move axially forward.

As shown best in FIGS. 3-4A, the bearing 40 defines a substantially planar forward end 40c of the rod-shaped core 40a. Conversely, the inner closed end 42b of the collar 42 (opposite the outer open end of the collar 42) defines a convex surface facing toward the outer open end. The apex of the convex surface of the inner closed end 42b of the collar 42 contacts the substantially planar forward end 40c of the bearing 40 when the collar 42 snaps onto the bearing 40. Accordingly, contact between the collar 42 and the bearing 40 is advantageously minimized to reduce rotational friction generated during rotation of the first shaft 20. As should be understood by those of ordinary skill in the art, the closed end of the collar 42 may alternatively define the substantially planar surface and the end surface 40c of the bearing 40 may define the convex surface facing toward the closed end 42b of the collar 42 to achieve the same contact relationship between the bearing 40 and the collar 42.

As shown in FIG. 4B, the first sleeve 26 may alternatively include the elastically expandable collar 42 projecting axially forward into the first sleeve 26 from the rear end thereof, and the first shaft 20 may include the corresponding bearing 40 projecting axially rearwardly from the rear end of the first shaft 20. The closed end 42b of the collar 42 may define a substantially planar surface and the end surface 40c of the bearing 40 may define a convex surface facing toward the closed end 42b of the collar 42 to achieve the same contact relationship between the bearing 40 and the collar 42. As should be understood by those of ordinary skill in the art, however, the bearing 40 may define the substantially planar end surface 40c and the closed end 42b of the collar 42 may define the convex surface facing toward the planar end surface 40c of the bearing 40.

As shown in FIGS. 1-3, the second sleeve 28 of the chassis 12 defines at least partially open front and rear ends, such that the actuator 14 secured therein may engage other operational components at either end. An actuator gear 14b of the actuator 14, positioned adjacent the rear end of the second sleeve 28 when the actuator 14 is secured within the sleeve 28 engages the transmission gear 18. The first shaft 20 further includes a telescoping assembly rotation gear 44 adjacent the inner closed end 42b of the collar 42. The transmission gear 18 engages the rotation gear 44 via an opening 46 in the first sleeve 26. Accordingly, the actuator 14 is operatively engaged with the telescoping driving assembly 16.

In operation, the actuator 14, the telescoping driving assembly 16 and the transmission gear 18 are secured within the chassis 12 in the manner previously disclosed. When secured to the chassis 12, the actuator 14 is operatively engaged with the telescoping driving assembly 16 such that rotation of the actuator gear 14b drives the telescoping driving assembly 16. The telescoping driving assembly 16 is aligned with the bay/track for the cartridge 54 when the modular drive train 10 is secured to the housing 52. Once the cartridge 54 is inserted in the bay/track thereof, and the injector 50 is activated, the actuator 14 drives the telescoping driving assembly 16 to expand, engage and advance the piston 54a through the cartridge 54 to expel substance therefrom.

Advantageously, the actuator 14, the telescoping driving assembly 16 and the transmission gear 18 may each be inserted axially into the chassis 12 without tools (as explained above via the respective snap mechanisms). Further advantageously, assembly of the drive train 10 may be performed outside of the injector 50, and the assembled drive train 10 may be secured into the injector 50 as a single modular unit. Yet further advantageously, the telescoping driving assembly 16, the transmission gear 18 and the chassis 12 may be constructed of molded polymeric, e.g., plastic parts.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention, as set forth in the appended claims.

We claim:

1. A drive train for an injector configured to receive a cartridge therein, wherein the cartridge is sealed at one end by a piston, the drive train comprising:
   a chassis securable within the injector and having a first engagement member; and
   a telescoping driving assembly mounted within the chassis, the telescoping driving assembly comprising:
      a first shaft rotatable relative to the chassis and having a second engagement member, and
      a second shaft telescopically connected to the first shaft and axially movable relative to the first shaft, wherein rotation of the first shaft axially drives the second shaft from a retracted configuration to an extended configuration to advance the piston within the cartridge, and the second shaft is rotatably fixed relative to the chassis,
   wherein the second engagement member comprises an elastically deflectable collar projecting axially rearwardly from a rear end of the first shaft, and wherein engagement of the first engagement member and the second engagement member axially secures the first shaft to the chassis and permits rotation of the first shaft relative to the chassis.

2. The drive train of claim 1, wherein the first engagement member includes at least one radially projecting tab configured to interfere with the second engagement member.

3. The drive train of claim 1, wherein the elastically deflectable collar comprises a plurality of angularly spaced arcuate members.

4. The drive train of claim 1, wherein the chassis comprises a first sleeve, the first engagement member projects axially into the first sleeve, and the telescoping driving assembly is received within the first sleeve.

5. The drive train of claim 4, wherein the second shaft is rotationally fixed to the first sleeve.

6. The drive train of claim 1, further comprising:
   an actuator configured to rotate the first shaft of the telescoping driving assembly,
   wherein the chassis further comprises a second sleeve that receives the actuator.

7. The drive train of claim 6, wherein the second sleeve and the actuator include complementary snap connection components that secure the actuator in the second sleeve.

8. The drive train of claim 6, further comprising a transmission gear connecting the actuator and the first shaft of the telescoping driving assembly.

9. The drive train of claim 1, wherein the telescoping driving assembly further comprises:
   a third shaft connecting the first shaft with the second shaft, the third shaft being threadedly connected to the first shaft and threadedly connected to the second shaft, the third shaft being rotatable and axially movable relative to the first shaft and the second shaft being axially movable relative to the first and third shafts, and
   an anti-rotation sleeve being rotationally fixed and axially slidable relative to the chassis and rotationally fixed and axially slidable relative to the second shaft.

10. A drive train for an injector configured to receive a cartridge, wherein the cartridge is sealed at one end by a piston, the drive train comprising:
   a telescoping driving assembly comprising:
      a first shaft, and
      a second shaft telescopically connected with the first shaft and axially movable relative to the first shaft, wherein rotation of the first shaft axially drives the second shaft from a retracted configuration to an extended configuration to advance the piston within the cartridge, the second shaft being rotatably fixed;
   an actuator configured to rotate the first shaft of the telescoping driving assembly; and
   a chassis securable within the injector, the chassis comprising:
      a first sleeve, wherein the telescoping driving assembly is received within the first sleeve and the first shaft is axially secured to the first sleeve, and
      a second sleeve generally parallel to the first sleeve, wherein the actuator is received within the second sleeve.

11. The drive train of claim 10, further comprising a transmission gear connecting the actuator and the first shaft of the telescoping driving assembly.

12. The drive train of claim 11, wherein the first shaft includes a rotation gear, the first sleeve includes an opening, and the transmission gear engages the rotation gear through the opening.

13. The drive train of claim 11, wherein the second sleeve includes an open rear end, the actuator including an actuator gear positioned adjacent the open rear end, and the actuator gear engages the transmission gear.

14. The drive train of claim 10, wherein the second sleeve and the actuator include complementary snap connection components that secure the actuator in the second sleeve.

15. The drive train of claim 10, wherein the first shaft includes a first engagement member, the first sleeve includes a second engagement member, and engagement of the first engagement member and the second engagement member axially secures the first shaft to the first sleeve and permits rotation of the first shaft relative to the chassis.

16. The drive train of claim 15, wherein one of the first and second engagement members includes at least one radially projecting tab.

17. The drive train of claim 1, wherein the second shaft includes a rib, the chassis includes a slot, and the rib is received in the slot to rotatably fix the second shaft relative to the chassis.

18. The drive train of claim 8, wherein the first shaft includes a rotation gear, the chassis includes an opening, and the transmission gear engages the rotation gear through the opening.

19. The drive train of claim 15, wherein one of the first and second engagement members includes a collar comprising a plurality of angularly spaced arcuate members.

20. The drive train of claim 1, wherein the first engagement member comprises a bearing, and the elastically deflectable collar is configured to receive the bearing.

21. The drive train of claim 1, wherein the second engagement member is configured to snap over the first engagement member to engage the first engagement member and the second engagement member.

22. An injector comprising:
   a housing configured to receive a cartridge; and
   the drive train of claim 1 secured within the housing.

23. An injector comprising:
   a housing configured to receive a cartridge; and
   the drive train of claim 10 secured within the housing.

* * * * *